(12) United States Patent
Beyaert et al.

(10) Patent No.: US 8,309,523 B2
(45) Date of Patent: Nov. 13, 2012

(54) INHIBITORS OF MALT1 PROTEOLYTIC ACTIVITY AND USES THEREOF

(75) Inventors: Rudi Beyaert, Zingem (BE); Peter Marynen, Herent (BE); Thijs Baens, Lubbeek (BE); Karen Heyninck, Scheldewindeke (BE)

(73) Assignees: VIB VZW, Ghent (BE); Universiteit Gent, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 12/734,651

(22) PCT Filed: Nov. 20, 2008

(86) PCT No.: PCT/EP2008/065925
§ 371 (c)(1),
(2), (4) Date: Oct. 1, 2010

(87) PCT Pub. No.: WO2009/065897
PCT Pub. Date: May 28, 2009

(65) Prior Publication Data
US 2011/0021548 A1    Jan. 27, 2011

Related U.S. Application Data

(60) Provisional application No. 61/004,097, filed on Nov. 21, 2007.

(30) Foreign Application Priority Data

Nov. 21, 2007  (EP) ..................................... 07121200

(51) Int. Cl.
*A61K 38/00*    (2006.01)
*A61P 35/00*    (2006.01)

(52) U.S. Cl. ..................... 514/19.2; 514/18.9; 514/19.6; 530/330

(58) Field of Classification Search .................. 514/270; 544/300
See application file for complete search history.

(56) References Cited

U.S. PATENT DOCUMENTS
2004/0110145 A1 *  6/2004  Bennett et al. .................... 435/6

FOREIGN PATENT DOCUMENTS
WO    WO 03074497 A1 *  9/2003

OTHER PUBLICATIONS

P.G.W. Gettins, Chemical Reviews, 102, 4751-4803 (2002).*
A. Sucharda-Sobczyk et al., European Journal of Biochemistry, 96, 131-139 (1979).*

* cited by examiner

*Primary Examiner* — James O Wilson
*Assistant Examiner* — Alexander R Pagano
(74) *Attorney, Agent, or Firm* — TraskBritt

(57) ABSTRACT

The present invention relates to inhibitors of MALT1 proteolytic and/or autoproteolytic activity. More specifically, it relates to compounds such as, but not limited to peptide derivates such as Z-LSSR-CHO (see SEQ ID NO:1), Z-LSSR-CMK (see SEQ ID NO:1), Z-GASR-CHO (see SEQ ID NO:2), and Z-GASR-CMK (see SEQ ID NO:2), and small compounds such as 5-{[5-(3-chloro-4-methylphenyl)-2-furyl]methylene}-2-thioxodihydro-4,6(1H,5H)-pyrimidinedione and variants thereof, and the use of those compounds for the preparation of a medicament. The invention relates further to a method to screen for inhibitors of the MALT1 proteolytic and/or autoproteolytic activity.

3 Claims, 20 Drawing Sheets

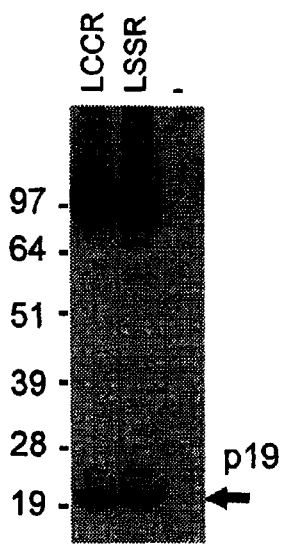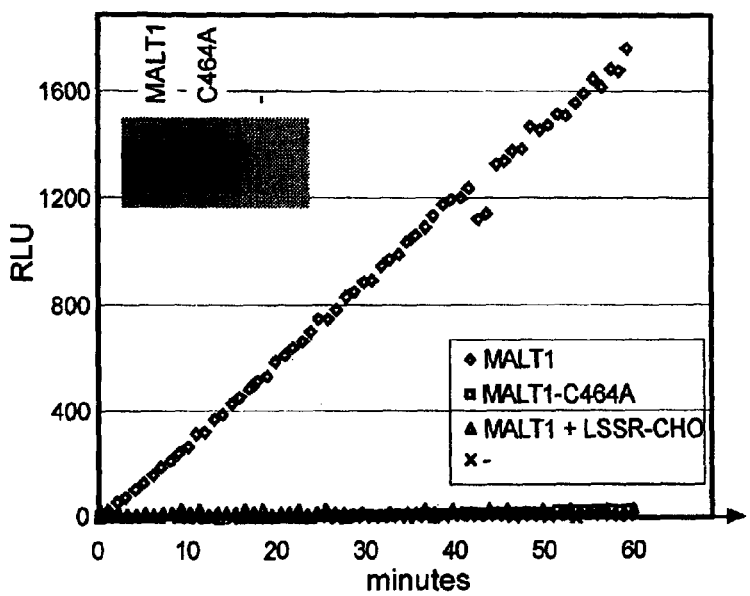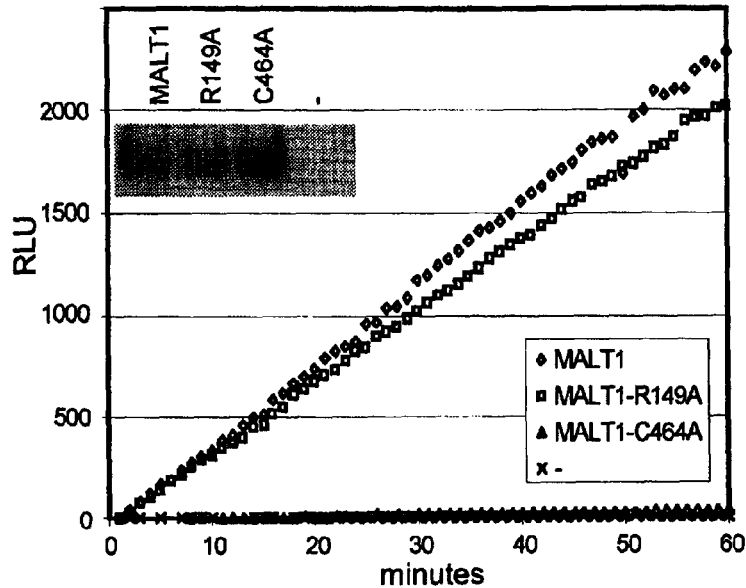
FIG. 3 (1 of 2)

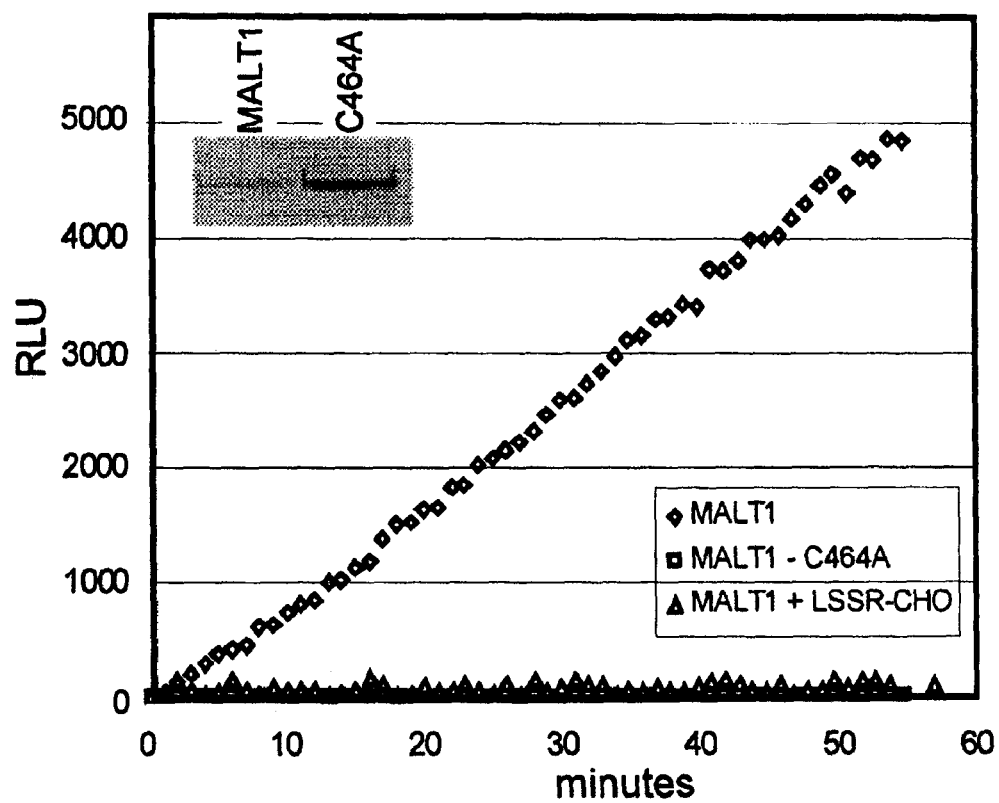
FIG. 3 (2 of 2)

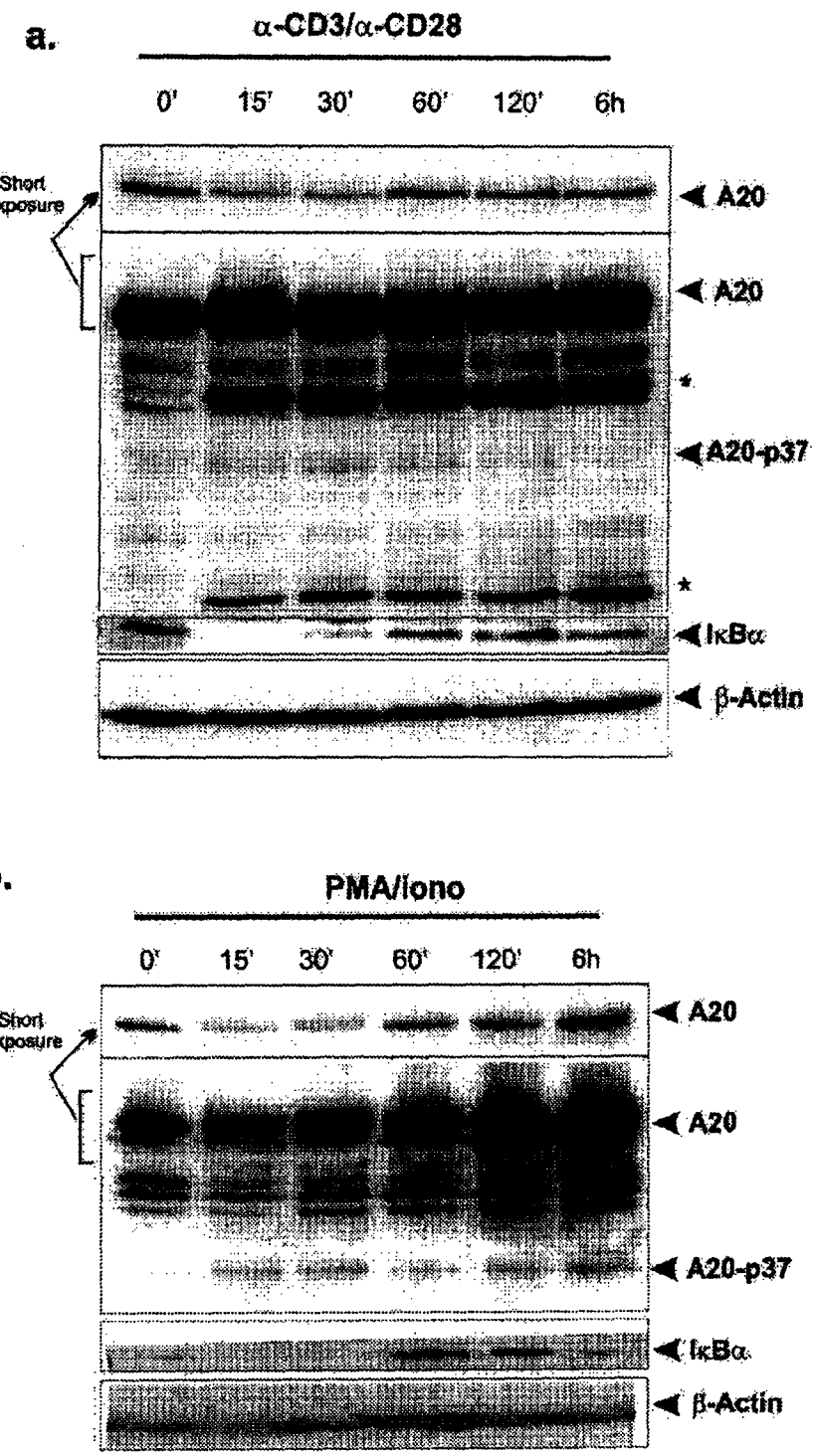
FIG. 6 (1 of 3)

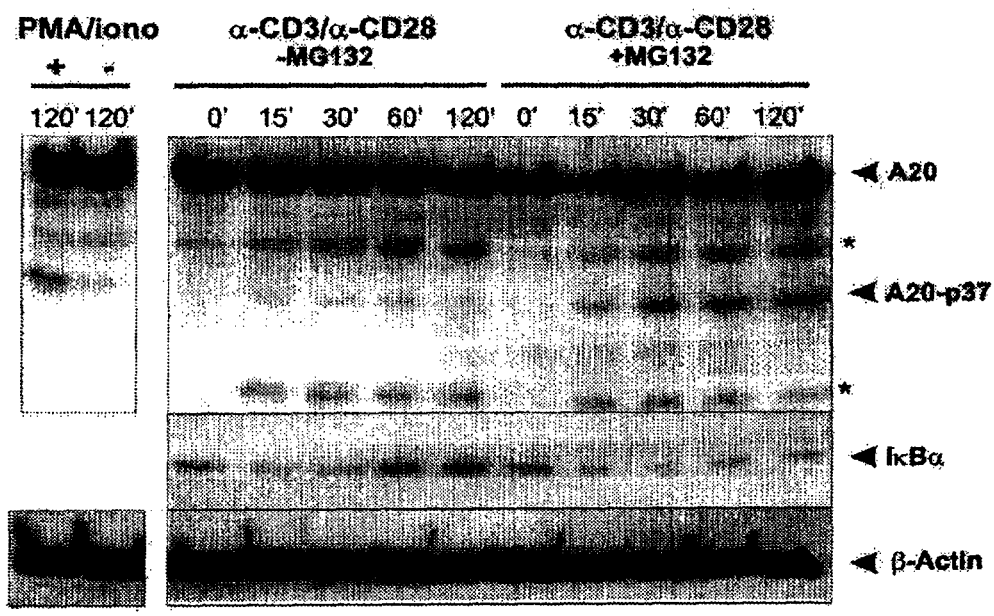
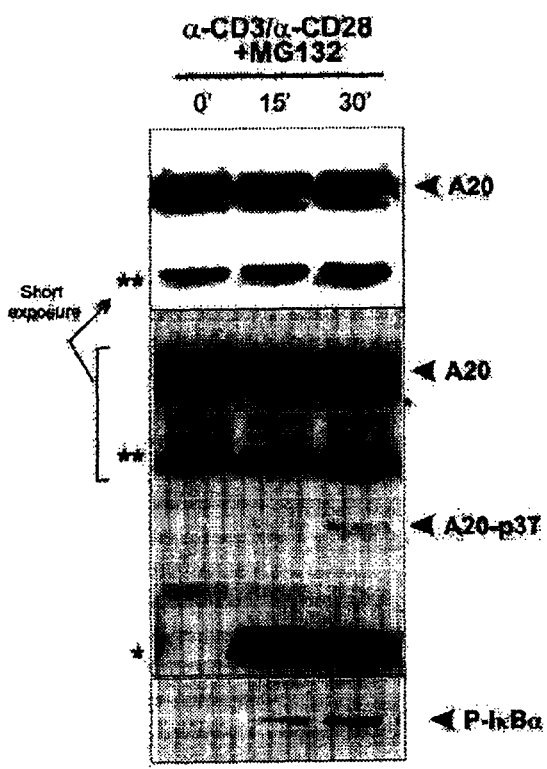
FIG. 6 (2 of 3)

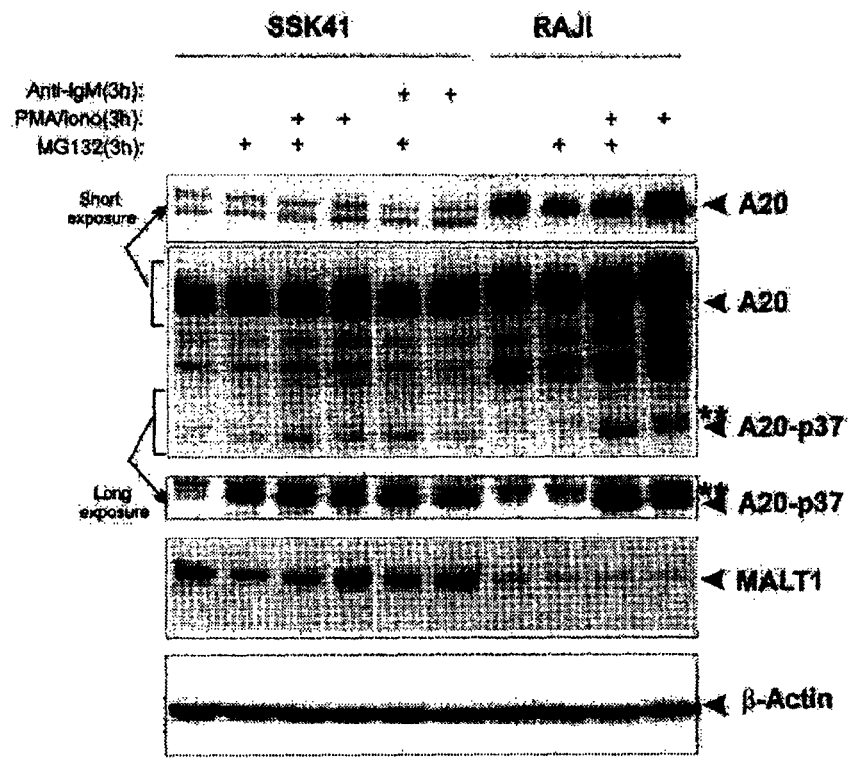
FIG. 6 (3 of 3)

a.
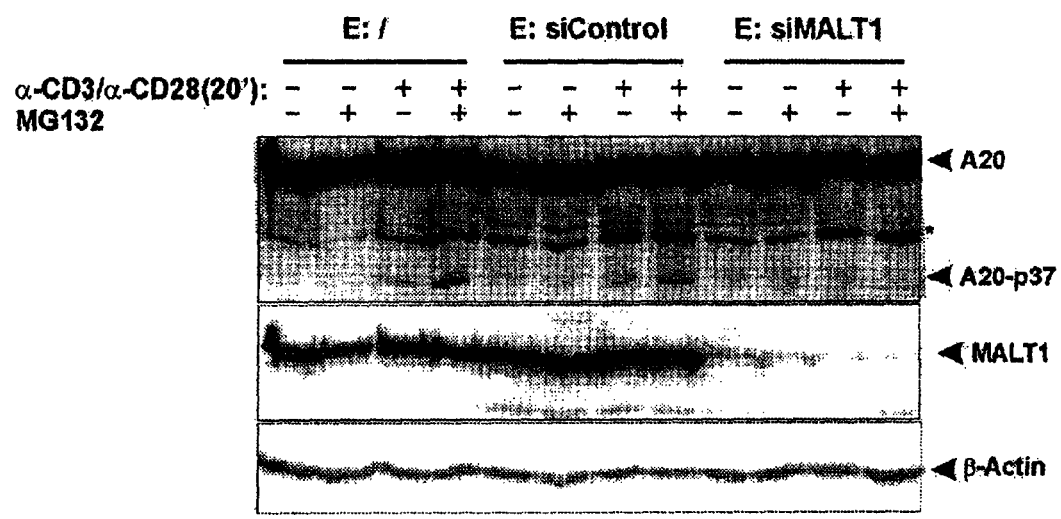
b.
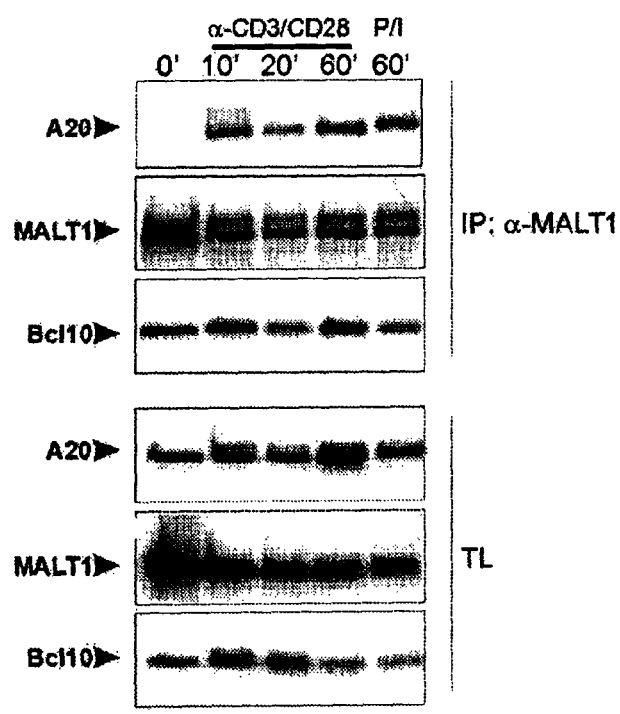
FIG. 7 (1 of 3)

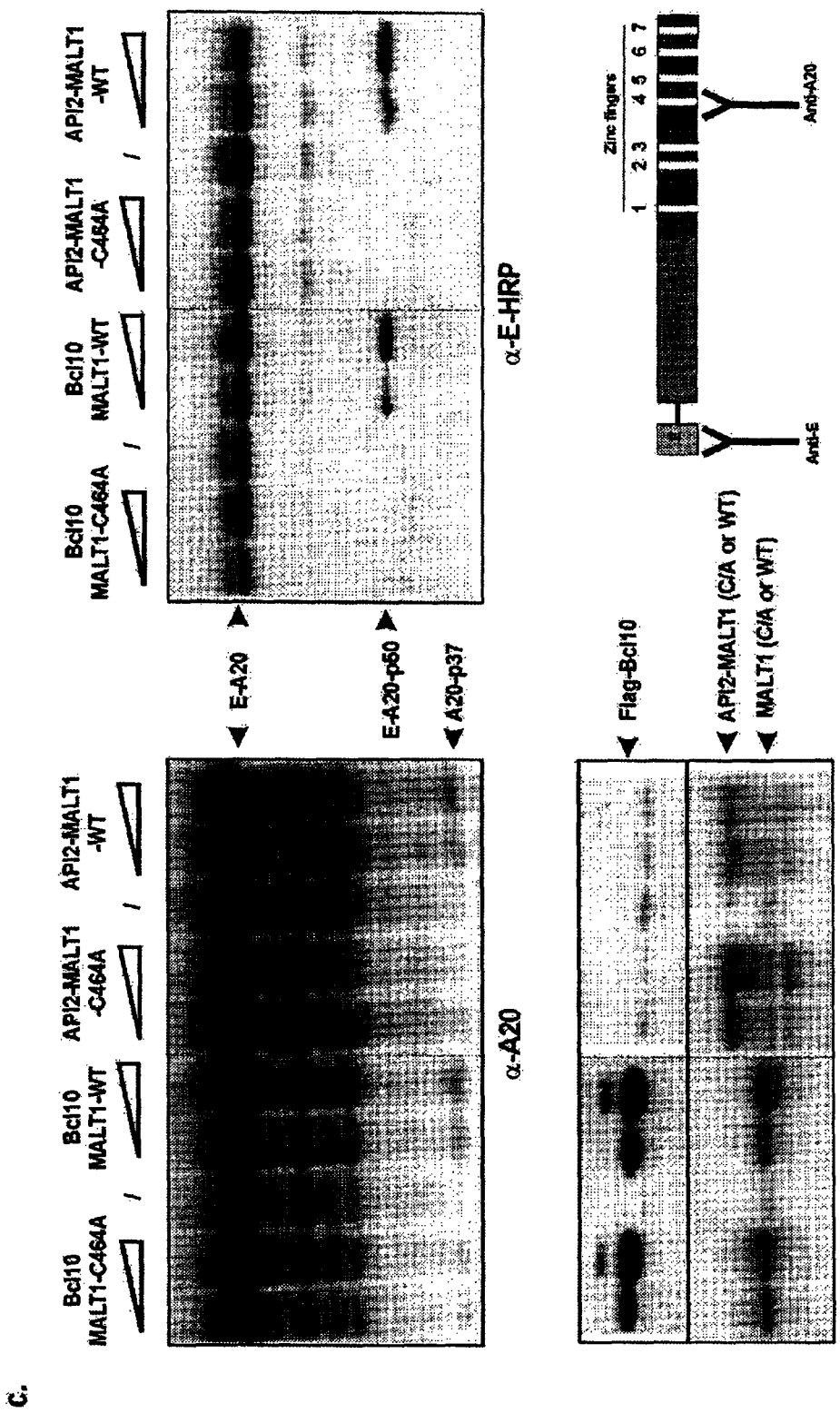
FIG. 7 (2 of 3)

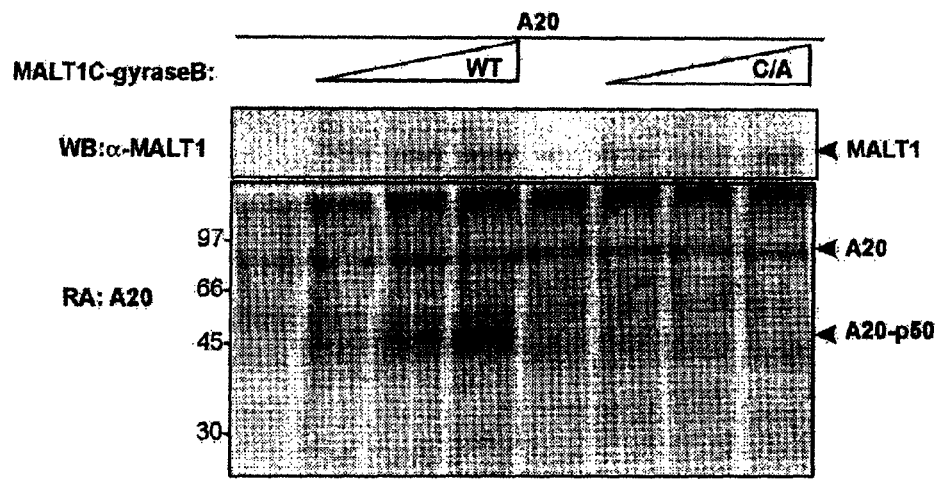
FIG. 7 (3 of 3)

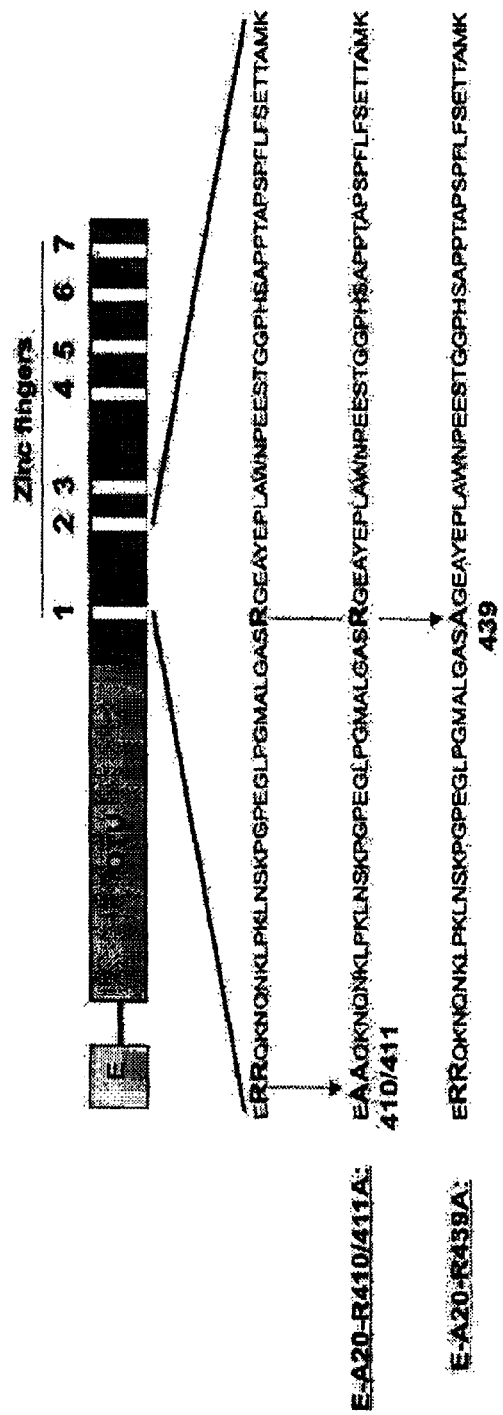
FIG. 8 (1 of 2)

b.
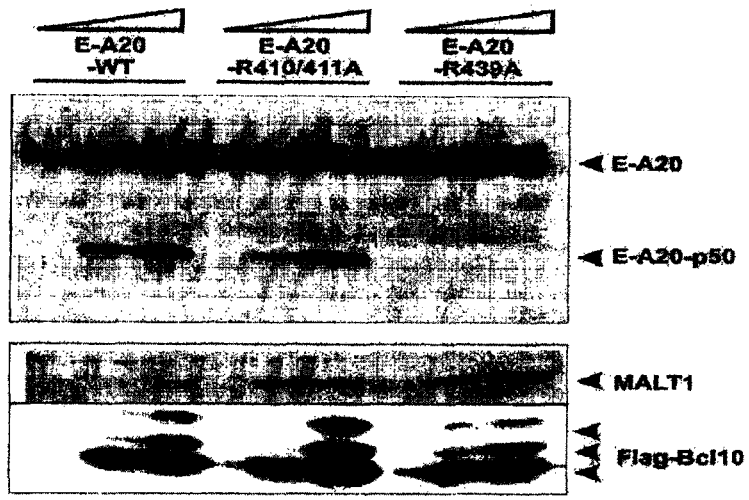
c.
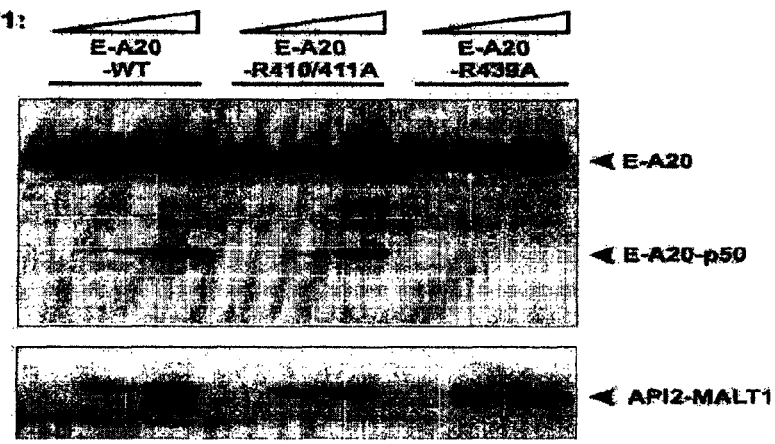
FIG. 8 (2 of 2)

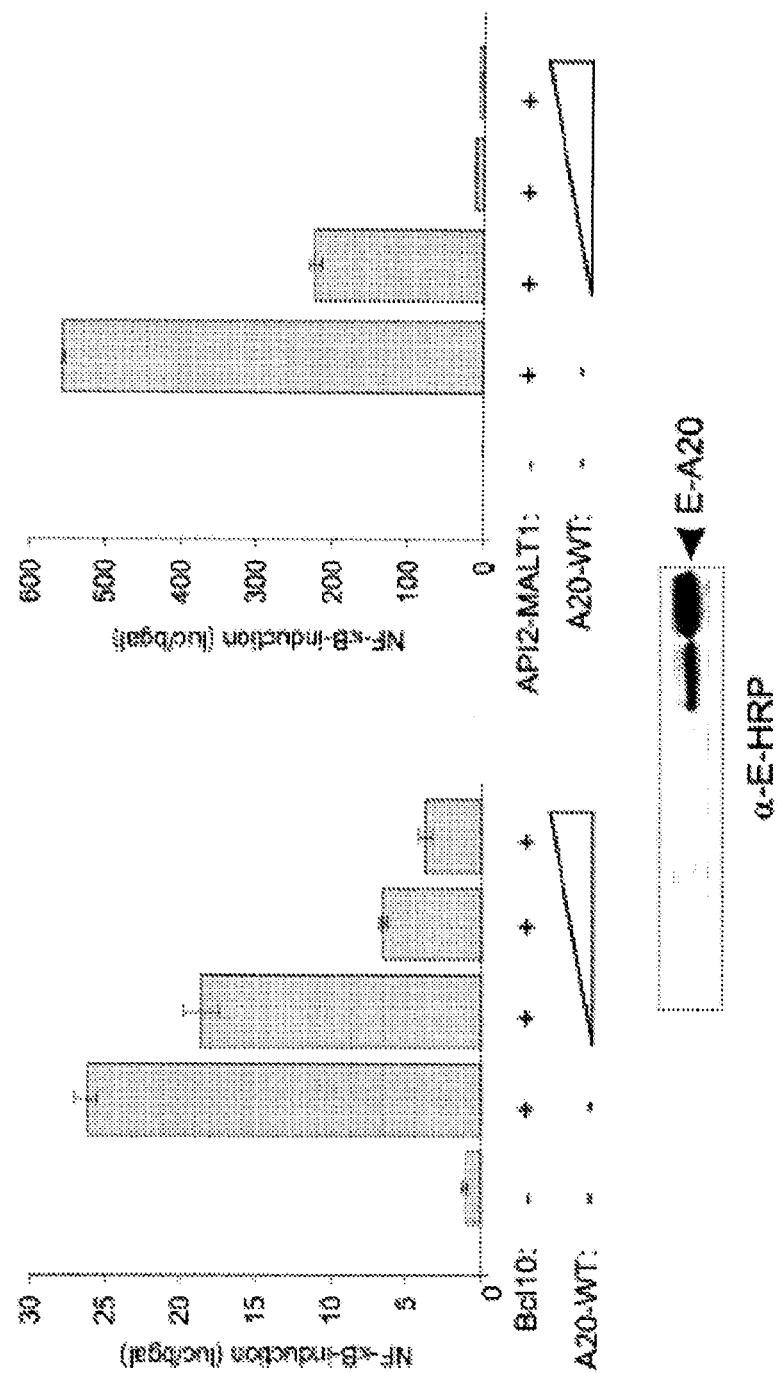
FIG. 9 (1 of 3)

B.
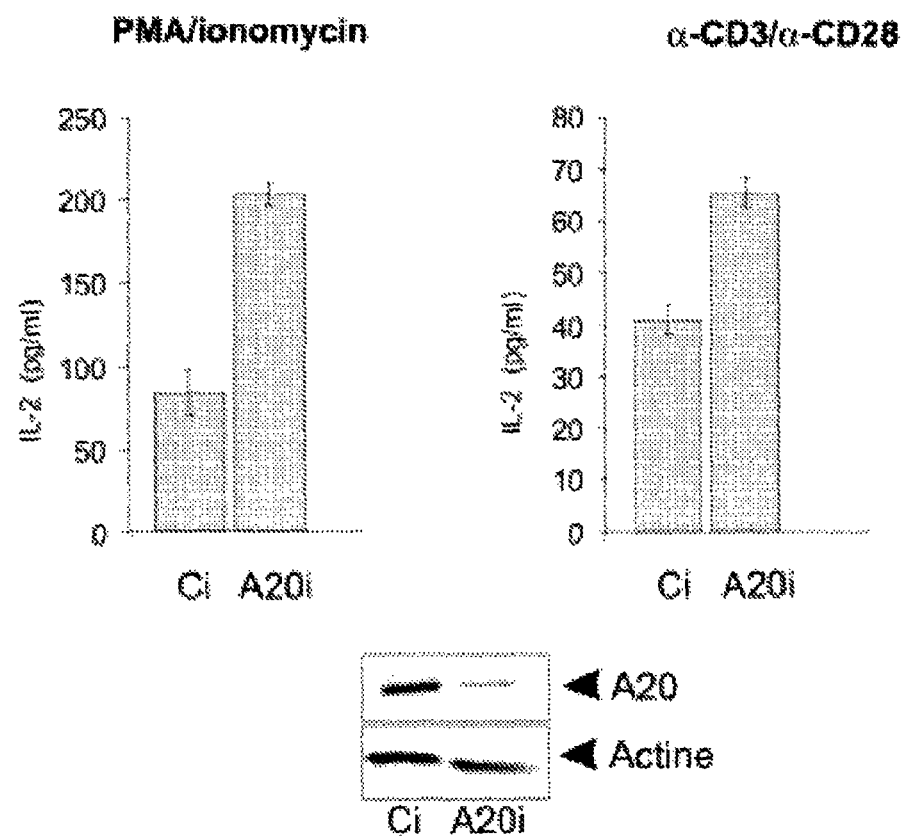
FIG. 9 (2 of 3)

c.
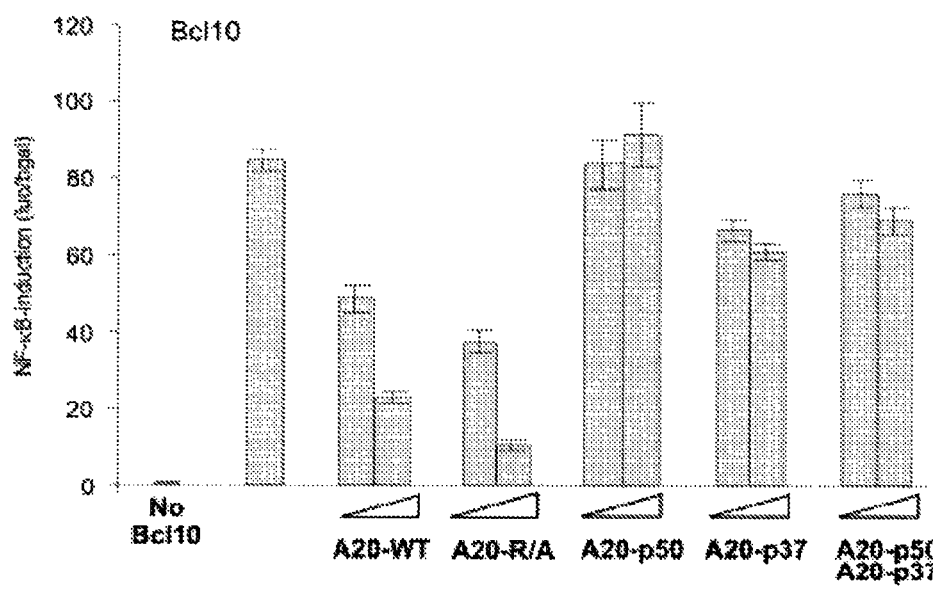
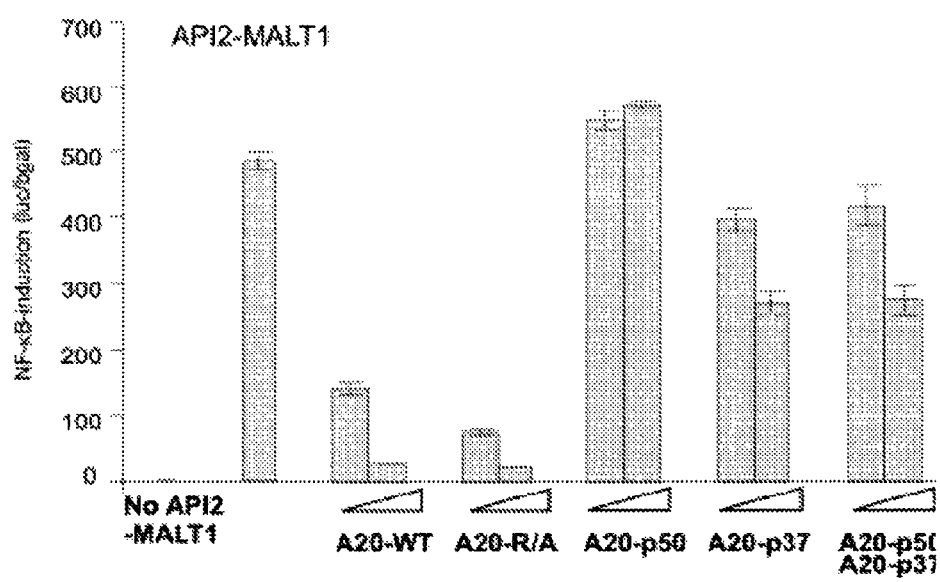
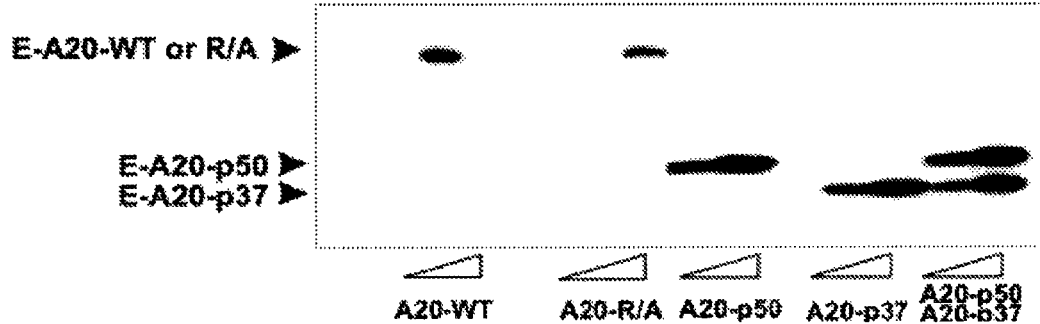
FIG. 9 (3 of 3)

A.
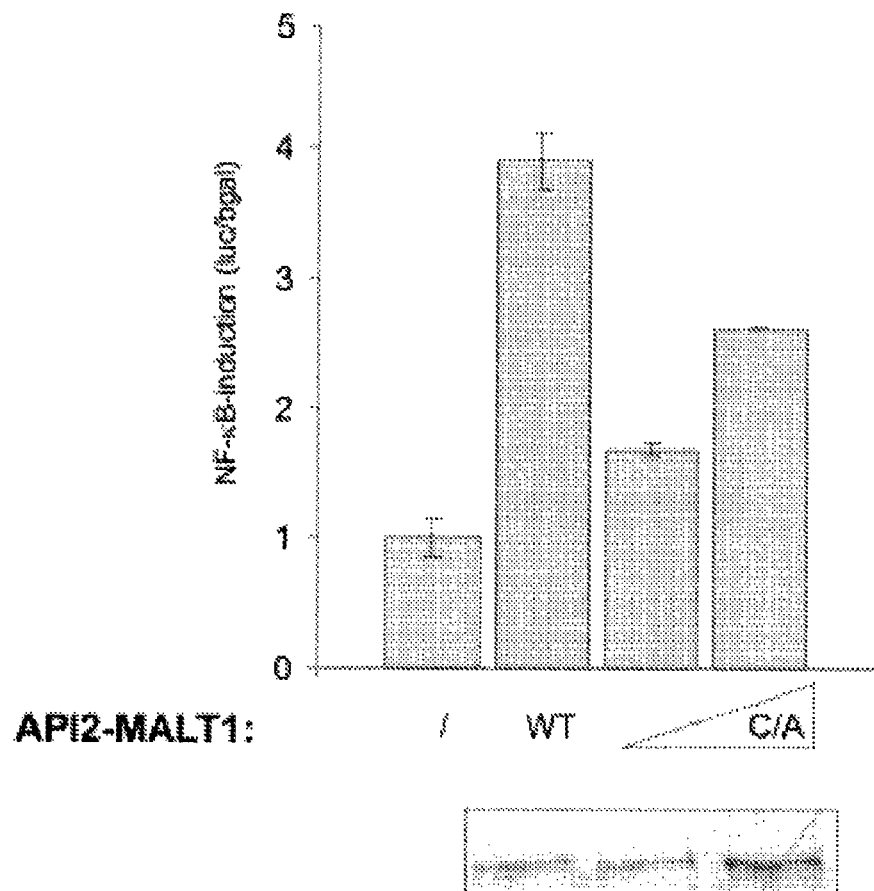
FIG. 10 (1 of 2)

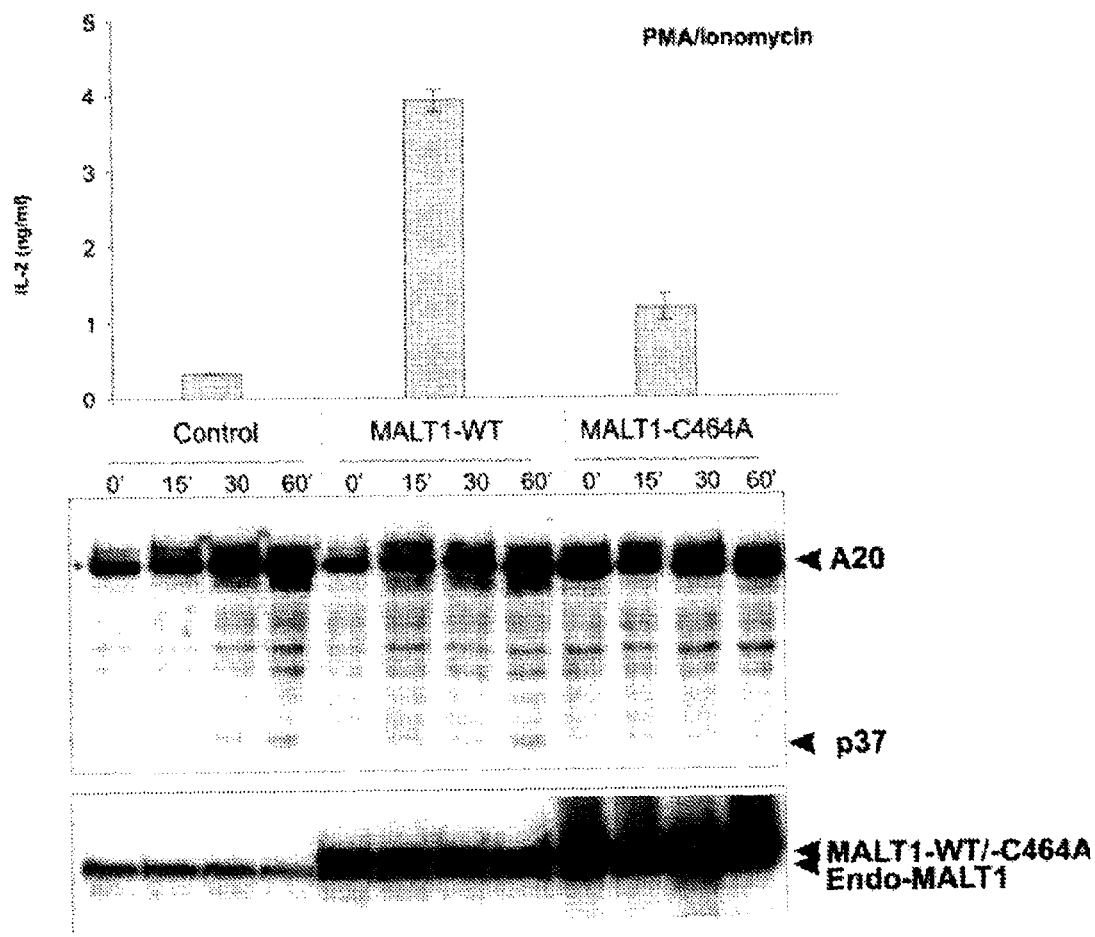
FIG. 10 (2 of 2)

INHIBITORS OF MALT1 PROTEOLYTIC ACTIVITY AND USES THEREOF

CROSS-REFERENCE TO RELATED APPLICATIONS

This is a national phase entry under 35 U.S.C. §371 of International Patent Application PCT/EP2008/065925, filed Nov. 20, 2008, published in English as International Patent Publication WO 2009/065897 A2 on May 28, 2009, which claims the benefit under Article 8 of the Patent Cooperation Treaty to European Patent Application Serial No. 07121200.5, filed Nov. 21, 2007, and U.S. Provisional Patent Application Ser. No. 61/004,097, filed Nov. 21, 2007 and under 35 U.S.C. §119(e) to U.S. Provisional Patent Application Ser. No. 61/004,097, filed Nov. 21, 2007.

TECHNICAL FIELD

The invention relates to inhibitors of MALT1 proteolytic and/or autoproteolytic activity. More specifically, it relates to compounds such as, but not limited to peptide derivates such as Z-LSSR-CHO (see SEQ ID NO:1), Z-LSSR-CMK (see SEQ ID NO:1), Z-GASR-CHO (see SEQ ID NO:2), and Z-GASR-CMK (see SEQ ID NO:2), and small compounds such as 5-{[5-(3-chloro-4-methylphenyl)-2-furyl]methylene}-2-thioxodihydro-4,6(1H,5H)-pyrimidinedione and variants thereof, and the use of those compounds for the preparation of a medicament. The invention relates further to a method to screen for inhibitors of the MALT1 proteolytic and/or autoproteolytic activity.

BACKGROUND

Studies in Bcl10-(Ruland et al., 2001) and Malt1-deficient (Ruland et al., 2003; Ruefli-Brasse et al., 2003) mice revealed their essential role in the signaling cascade from the antigen receptors to the transcription factor NFκB. Moreover, chromosomal translocations leading to overexpression of Bcl10 or MALT1, or creating the constitutively active fusion protein API2-MALT1, all result in uncontrolled and stimulus-independent activation of NFκB (Zhang et al., 1999, Willis et al., 1999, Dierlamm et al., 1999, Sanchez-Izquierdo et al., 2003). Furthermore, this constant activation of NFκB is thought to play a role in the pathogenesis of certain MALT-lymphomas. The human MALT1 protein contains a caspase p20-like domain, preceded by a large pro-domain, consisting of a Death Domain (DD) and two Ig-like domains, and is therefore also referred to as the human paracaspase (Uren et al., 2000). As such, MALT1 is most similar to initiator caspases that possess longer pro-domains than effector caspases, whose pro-domain is very small. Proteolytic activation of the initiator caspases in the apoptosome most likely occurs via a conformational change of the active site attained through direct interaction with the apoptosome or via proximity-driven oligomerization facilitated by the apoptosome (Boatright et al., 2003; Bao and Shi, 2007). Although Uren et al. (2000) suggested that in API2-MALT1 fusions paracaspase activity may play a role, they could not prove proteolytic activity. Moreover, mutation of the catalytic activity didn't abolish all NFκB activity. Indeed, the proteolytic activity of MALT1 paracaspase is not generally accepted and so far, no proteolytic activity has been reported for MALT1/paracaspase.

T-cell receptor (TCR) engagement results in the formation of a highly ordered, membrane-associated complex called supra-molecular activation cluster (SMAC). Lipid rafts, which are sphingolipid- and cholesterol-rich microdomains in the cell membrane, are suspected to play an important role herein, as they migrate to the centre of the SMAC (cSMAC) to form larger clusters that function as signaling platforms. TCR stimulation and CD28 co-stimulation both activate a cascade of tyrosine phosphorylation that converges at lipid raft association and activation of PKCθ. Activated PKCθ serves different functions. On the one hand, it recruits TAK1 and the IKK complex to the periphery of the SMAC, resulting in TAK1-mediated phosphorylation of IKKβ (Shambharkar et al., 2007; Lee et al., 2005). On the other hand, PKCθ phosphorylates CARMA1 residing in the lipid rafts (Sommer et al., 2005; Matsumoto et al., 2005). This evokes a conformational change of CARMA1, allowing the recruitment of additional CARMA1 molecules (Sommer et al., 2005), BCL10 (Wang et al., 2002; Hara et al., 2004) and MALT1 (Che et al., 2004) to the lipid rafts in the cSMAC. Oligomerization of CARMA1 (Rawlings et al., 2006) triggers oligomerization of the BCL10-MALT1 complex, which in turn induces the oligomerization and activation of TRAF6 proteins via Lys63-linked auto-polyubiquitination (Sun et al., 2004). These polyubiquitin chains might assist CARMA1-dependent recruitment of the IKK complex in the cSMAC (Hara et al., 2004; Stilo et al., 2004) via the ubiquitin binding domains of IKKγ (Wu et al., 2006), which then culminates in full IKK activation via Lys63-linked polyubiquitination of IKKγ (Zhou et al., 2004). Activated IKK phosphorylates the NFκB inhibitory protein IκB (Sun et al., 2004), which marks it for Lys48-linked polyubiquitination and degradation by the proteasome (Chen, 2005), thereby releasing and activating NFκB. Important, the BCL10 protein appears to be a point of divergence in the NFκB pathway in T- and B-lymphocytes (Ruland et al., 2003). Whereas mature T-cells depend entirely on MALT1 to send information from BCL10 to NFκB, mature B-cells require MALT1 only for a BCL10-subprogram by specifically inducing c-Rel upon B-cell receptor stimulation, while BCL10 regulates both RelA and c-Rel activation (Ferch et al., 2007).

Recent work also identified BCL10 and MALT1 as central regulators of a specific signaling pathway that controls NFκB activation and proinflammatory cytokine production upon Fc epsilon RI ligation on mast cells. Mice deficient for either protein display severely impaired IgE-dependent late phase anaphylactic reactions (Klemm et al., 2006). Strong evidence suggesting that conserved BCL10-MALT1 complexes interact with different CARD scaffolds to connect various receptors in different cell types to NF-kB signaling has emerged more recently. The CARD10 (CARMA3)-Bcl10-Malt1 signalosome functions as a link between G protein-coupled receptor (GPCR) signaling and proinflammatory NF-kB activation. For example, CARMA3/Bcl10/MALT1 dependent NF-kB activation mediates angiotensin II-responsive inflammatory signaling in nonimmune cells (Allister-Lucas et al., 2007). The pathway is similar to the pathway described in lymphocytes, but CARMA1, which is found chiefly in lymphocytes is replaced by a family member with a wider tissue distribution profile, CARMA3. Similarly, BCL10 and MALT1 are critically required for NFκB induction in response to GPCR stimulation by lysophosphatidic acid (LPA) (Klemm et al., 2007). Further, Dectin-1 receptor-induced NFκB activation in dendritic cells depends on CARD9-BCL10-MALT1, indicating a role in responses to fungal infection. These results identify CARD-BCL10-MALT1 signalosomes as pivotal regulators that link not only innate and adaptive immune responses, but also GPCR signaling, to the canonical NF-kB pathway (reviewed by Wegener and Krappmann, 2007).

Studies in cell lines show that overexpressed MALT1 by itself does not activate NFκB, whereas co-expression with BCL10 results in a synergistic effect on BCL10-mediated NFκB activation (Lucas et al., 2001). Current hypothesis is that BCL10 facilitates MALT1 oligomerization and activation of associated TRAF6 proteins (Sun et al., 2004). However, it was also shown that mutation of the predicted catalytic cysteine (C464A) reduced the synergism with BCL10 (Lucas et al., 2001), though proteolytic activity has not been demonstrated so far, and the mechanism by which the reduced activity is caused was unknown till now.

Surprisingly we found that MALT1 shows proteolytic activity in vitro, with cysteine protease activity and that this activity can be detected using a tetrapeptide substrate. Co-expression of MALT1 and BCL10 or raft association of MALT1 induce its auto-proteolytic cleavage generating a 76 kDa C-terminal fragment that can activate NFκB signaling. Furthermore we demonstrate that MALT1 auto-proteolysis is involved in NFκB signaling. Moreover, we found that MALT1 proteolytic activity is activated upon TCR stimulation. More specifically, we demonstrated that MALT1 mediates the rapid proteolytic cleavage and inactivation of the NFκB inhibitor A20 (also known as TNFAIP3) upon TCR stimulation, resulting in increased TCR dependent IL-2 production.

DISCLOSURE OF THE INVENTION

A first aspect of the invention is an inhibitor of the MALT1 proteolytic and/or autoproteolytic activity. The inhibitor can be any inhibitor that inhibits the proteolytic activity of MALT1 at protein level. Preferably, the inhibitor is specific for the MALT1 proteolytic activity. As a non-limiting example, the inhibitor can be a protein, such as a serpin, it can be a peptide or a peptide derivate such as Z-LSSR-CHO (see SEQ ID NO:1), Z-LSSR-CMK (see SEQ ID NO:1), Z-GASR-CHO (see SEQ ID NO:2) or Z-GASR-CMK (see SEQ ID NO:2), or it can be a small chemical compound, such as 5-{[5-(3-chloro-4-methylphenyl)-2-furyl]methylene}-2-thioxodihydro-4,6(1H,5H)-pyrimidinedione. Inhibitors can be identified with the screening method according to the invention, as described below. In one preferred embodiment, the inhibitor is 5-{[5-(3-chloro-4-methylphenyl)-2-furyl]methylene}-2-thioxodihydro-4,6(1H,5H)-pyrimidinedione or a variant thereof. Indeed, it is clear for the person skilled in the art that, on the base of this molecule, variants can be developed with similar or even higher inhibitory activity. One group of variants are those in which the Cl groups have been replaced by another halogen atom, or where the halogen is placed in the 2, 5 or 6 position of the methylphenyl ring, possibly in combination with another halogen on the ring. Specially preferred is the embodiment where the inhibitor is 5-{[5-(3-chloro-4-methylphenyl)-2-furyl]methylene}-2-thioxodihydro-4,6(1H,5H)-pyrimidinedione. In another preferred embodiment, the inhibitor is selected from the group consisting of Z-LSSR-CHO (see SEQ ID NO:1), Z-LSSR-CMK (see SEQ ID NO:1), Z-GASR-CHO (see SEQ ID NO:2) and Z-GASR-CMK (see SEQ ID NO:2).

Another aspect of the invention is the use of an inhibitor according to the invention as a medicament.

Still another aspect of the invention is the use of an inhibitor according to the invention for the preparation of a medicament to treat diseases selected from the group consisting of hypertension, diabetic nephropathy, congestive heart failure, sepsis due to infection, preferably fungal infection, IgE-mediated diseases such as anaphylaxis and T-cell and/or B-cell receptor linked diseases. Preferably the inhibitor according to the invention is used for the preparation of a medicament to treat T-cell and/or B-cell receptor linked diseases. A T-cell or B-cell receptor linked disease is a disease caused by a pathological activation of the receptor, and includes, but is not limited to constitutive activation of the receptor. Preferably, the disease is a disease caused by pathological T-cell receptor-induced IL-2 production. T-cell and B-cell receptor linked diseases are known to the person skilled in the art and include, but are not limited to cancer, lymphoma (preferably marginal zone lymphoma) graft versus host disease, rheumatoid arthritis, multiple sclerosis and asthma.

Another aspect of the invention is the use of an inhibitor according to the invention for the preparation of a medicament to induce immunotolerance.

Still another aspect of the invention is a method to screen for inhibitors of MALT1 proteolytic and/or autoproteolytic activity, comprising: (a) contacting purified MALT1 with its substrate; (b) bringing the MALT1/substrate mixture in contact with a test compound; and (c) comparing the digestion of the substrate in the presence and absence of the compound. Preferably, the substrate comprises a tetrapeptide, even more preferably it comprises a tetrapeptide selected from the group consisting of LSSR (SEQ ID NO:1) and LCCR (SEQ ID NO:15). One preferred embodiment is a substrate selected from the group consisting of Ac-LSSR-AMC (see SEQ ID NO:1) and Ac-LCCR-AMC (see SEQ ID NO:15). Another preferred embodiment is an immobilized substrate, comprising a tetrapeptide according to the invention, whereby a fluorescent group is released upon hydrolysis of the peptide.

FIG. 3: Ac-LSSR-AMC (see SEQ ID NO:1) cleavage by precipitated and recombinant MALT1. Panel A) Functional replacement of the LCCR (SEQ ID NO:15) cleavage site of MALT1 by LSSR (SEQ ID NO:1). Arrow indicates the generated p19 fragment. Panel B) Fluorescence release (RLU) due to Ac-LSSR-AMC (see SEQ ID NO:1) cleavage (100 µM) in vitro by bio-IP purified MALT1 (◇) and the C464A (□) mutant. Addition of Z-LSSR-CHO (see SEQ ID NO:1) (100 µM) inhibits MALT1 proteolytic activity (Δ). (x) activity of bio-IPs from cells transfected with BirA only. Insert: immunoblot showing equal amounts of bio-IP purified MALT1 and the C464A mutant. Panel C) Fluorescence increase (RLU) due to Ac-LSSR-AMC (see SEQ ID NO:1) cleavage (100 µM) in vitro by bio-IP purified MALT1 (◇) and the R149A (□) or C464A (Δ) mutants Insert: immunoblot showing equal purification (X) birA only bio-IP. Panel D) Recombinant MALT1, but not the C464A mutant (Sun et al., 2004), cleaves Ac-LSSR-AMC (see SEQ ID NO:1) (100 µM) in vitro and its proteolytic activity is completely blocked by Z-LSSR-CHO (see SEQ ID NO:1) (100 µM). Insert: Coomassie stain showing recombinant protein concentrations.

Figure 4:
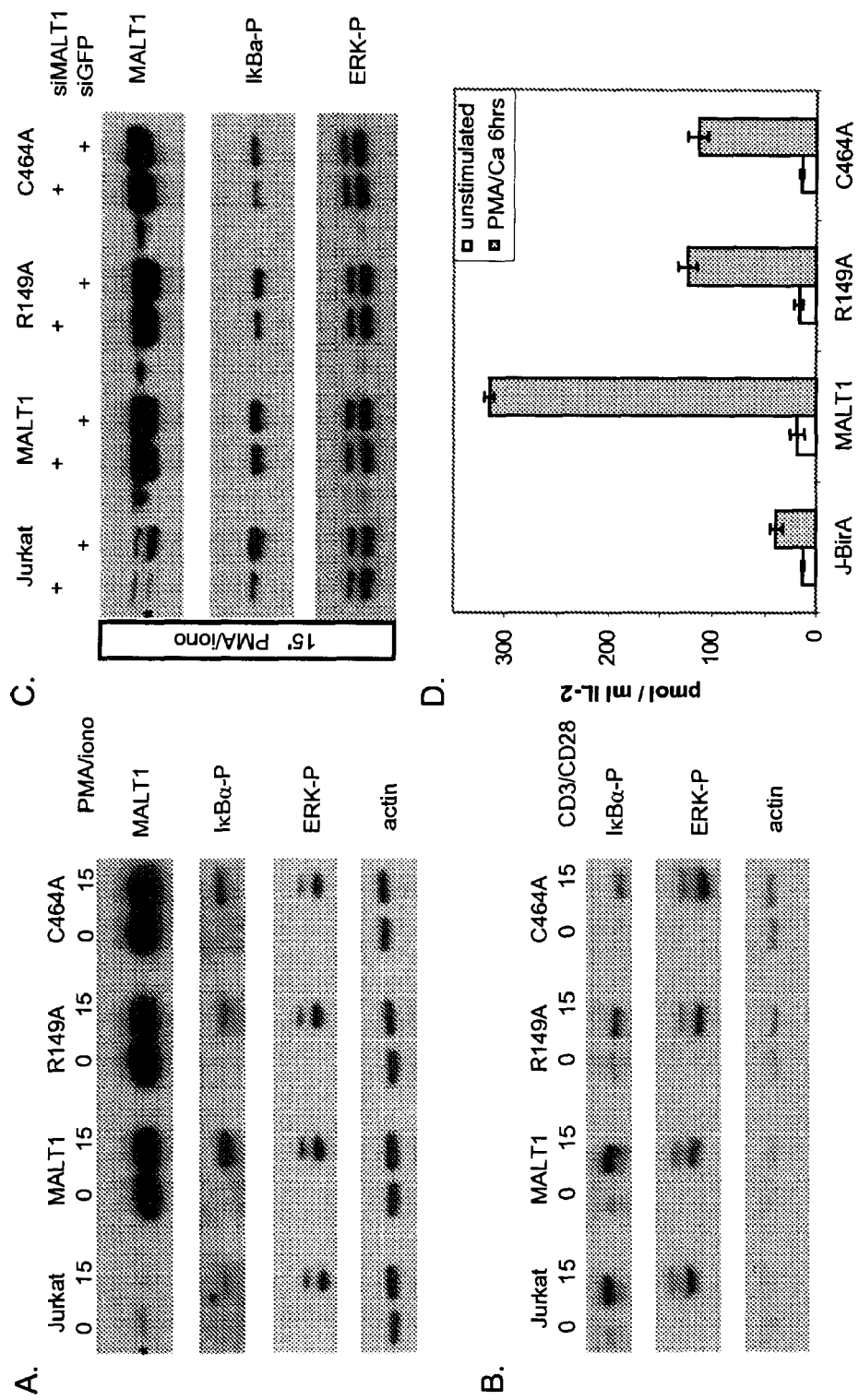

FIG. 4: MALT1 auto-proteolysis is involved in NFκB activation. Jurkat cells stably expressing MALT1, MALT1-R149A or MALT1-C464A were stimulated with Panel A) PMA/ionomycin or Panel B) Anti-CD3/-CD28 and phosphorylation of IκBα (activation of NFκB pathway) and ERK (activation is MALT1-independent) were analyzed by immunoblotting. β-actin expression levels show equal loading. (*): endogenous MALT1. Panel C) Phosphorylation of IκBα and ERK after PMA/ionomycin stimulation (15 minutes) of Jurkat cells stably expressing MALT1, MALT1-R149A or MALT1-C464A and pre-treated (18 hours) with siRNAs against the 3' UTR of MALT1. Panel D) IL-2 production of PMA/ionomycin treated Jurkat cells (6 hours) stably expressing MALT1, MALT1-R149A or MALT1-C464A. Data shown as mean+/−S.D. (n=3).

Figure 5:
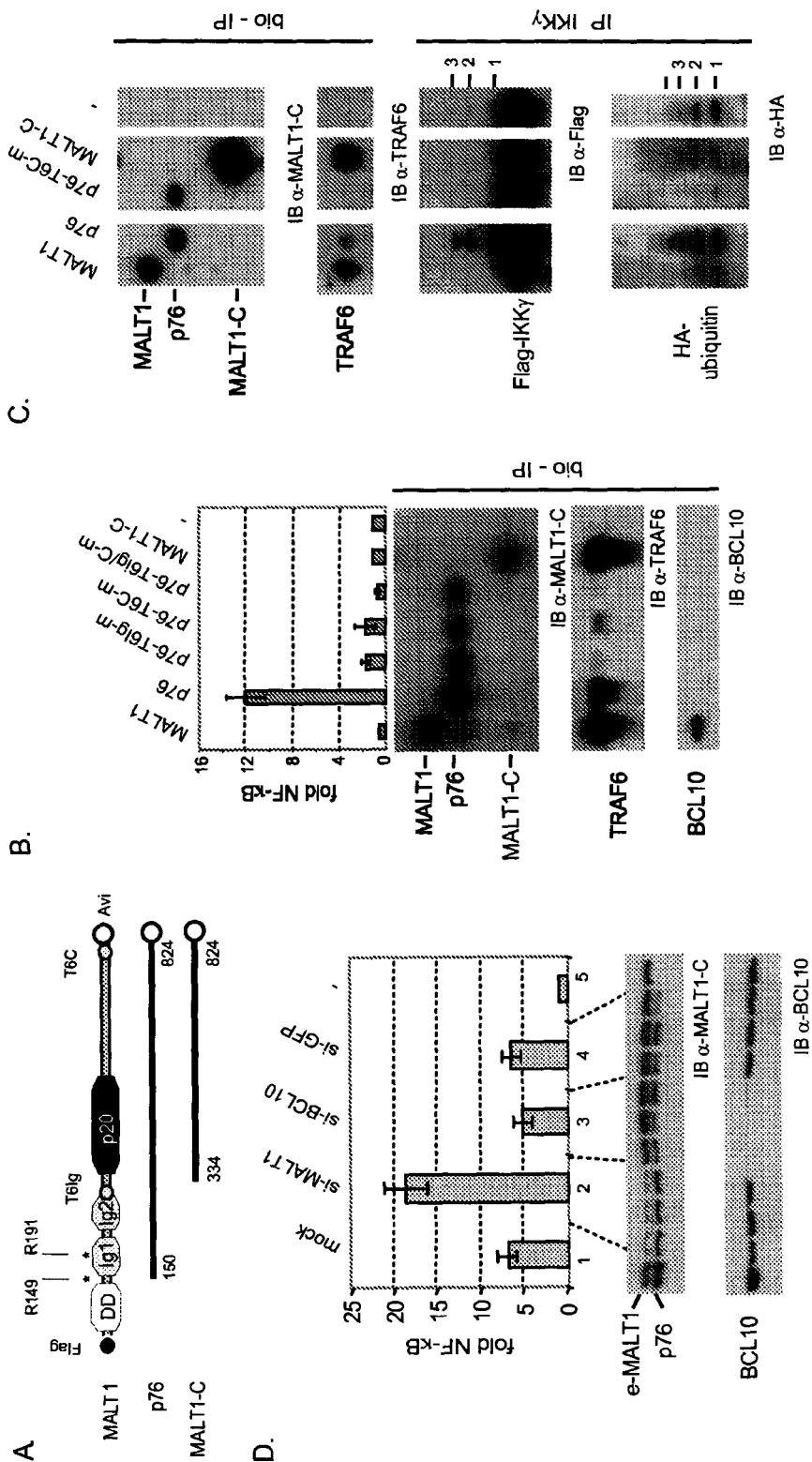

FIG. 5: p76 activates NFκB via TRAF6. Panel A) The structural domains of MALT1 plus the domain content (solid bars) of the p76 cleavage fragment and MALT1-C (Sun et al., 2004). Panel B) TRAF6 mediates NFκB signaling by p76. Top: NFκB-reporter assays of HEK293T cells transiently expressing MALT1, p76 and mutants or MALT1-C. Bottom: MALT1, p76 or MALT1-C, transiently expressed in HEK293T cells, were purified via bio-IPs and immunoblotted with anti-MALT1 (to show equal expression), anti-TRAF6 and anti-BCL10. Panel C) p76 induces polyubiquitination of IKKγ. Immunoblot analysis of bio-IP and IKKγ-IP of 293T cells transfected with pcD-F-IKKγ and pcd-HA-Ub in combination with indicated Avi-tagged MALT1 constructs. Panel D) BCL10 is not involved in NFκB signaling by p76. NFκB reporter assays of HEK-293T cells transfected with siRNA duplexes against MALT1, BCL10 or GFP (as control) followed by transient transfection with p76. The expression levels were determined by immunoblot with anti-MALT1 and anti-BCL10. NFκB-dependent luciferase activity (B/C) is shown as fold induction of vector-transfected cells and represents the mean+/−S.D. of three independent experiments.

FIG. 6: Generation of a 37 kDa protein fragment of A20 upon activation of T and B-cells. Jurkat cells (Panels a-c), primary human T-cells (Panel d), or SSK41 and Raji cells (Panel e) were stimulated for different times with respectively anti-CD3/anti-CD28, PMA/ionomycin, or anti-IgM. Where indicated, stimulation was done in the presence of 25 µM MG132 (30 min preincubation). A20, IκBα, pIκBα, MALT1 and β-actin expression were analyzed by western blotting. IκBα phosphorylation and degradation is indicative for the activation of the NFκB pathway. β-actin expression is included as a loading control. (*=heavy and light chains of the anti-CD3 or anti-CD28 antibodies used for stimulation; **non-specific band)

FIG. 7: MALT1 interacts with A20 and mediates its proteolytic cleavage. Panel a, Knockdown of MALT1 abrogates the anti-CD3/anti-CD28 induced cleavage of A20. Jurkat cells were mock electroporated (/) or electroporated with MALT1 siRNA (siMALT1) or control siRNA (siControl). Two days later, cells were stimulated for 20 min with anti-CD3/anti-CD28 with or without pretreatment with MG132. A20 cleavage was analyzed by immunoblotting (**=chains of the anti-CD3/anti-CD28 antibodies; overlapping with a non-specific band). Efficiency of MALT1 knockdown was analyzed by western blotting and immunodetection for MALT1 expression (middle panel). Western blotting for β-actin was performed as a loading control (bottom panel) Panel b, A20 interacts with MALT1 upon TCR-triggering. Jurkat cells were stimulated with anti-CD3/anti-CD28 or PMA/ionomycin for the indicate times. MALT1 was immunoprecipitated and co-immunoprecipitation of Bcl10 and A20 was analyzed by immunoblotting. (IP=immunoprecipitation; TL=total lysate) Panel c, MALT1-mediated cleavage of A20 depends on the catalytic site Cys464 of MALT1. HEK293T cells were transfected with E-A20 together with either wild type or catalytically inactive C/A mutants of API2-MALT1 or MALT1+Flag-Bcl10. N20 terminal and C-terminal fragments of A20 were detected by immunoblotting with anti-E-tag and anti-A20, respectively. Panel d, A20 is cleaved by recombinant MALT1 in vitro. Increasing concentrations (500, 1000 or 1500 nM) recombinant wild type (WT) MALT1C-gyraseB or the catalytically inactive mutant MALT1C-gyraseB-C464A (C/A) were in vitro incubated with [35S]methionine-labeled A20 for 1.5 h at 37° C. protein in a cosmotropic salt buffer. A20 and A20 cleavage was revealed by SDS-PAGE and autoradiography (lower panel). MALT1C-gyraseB levels were verified by Western blotting (upper panel).

FIG. 8: A20 is processed by MALT1 at R439 and contains SEQ ID NOS:6-8 sequentially. Panel a, Schematic overview of the domain structure of human A20. The potential cleavage site arginines are represented in bold. Panels b and c, Mutation of R439 in A20 abrogates its cleavage by MALT1 (b) or API2-MALT1 (c). E-A20 or the E-A20-R410/411A and E-A20-R439A mutants were overexpressed in HEK293T cells together with Flag-Bcl10/MALT1 or API2-MALT1. Cleavage of A20 was analyzed by immunoblotting with anti-E-tag.

FIG. 9: A20 cleavage by MALT1 disrupts its inhibitory effect on TCR-induced NFκB activation. Panel A, A20 overexpression inhibits Bcl10- or PMA/ionomycin-induced NFκB activation. HEK293T cells were transfected with Bcl10 (left panel) or API2-MALT1 (right panel), and increasing concentrations of A20. Twenty-four hours later, NFκB activation was measured. Panel B, Knockdown of A20 in Jurkat cells potentiates TCR-induced IL-2 production. Jurkat cells that were mock-electroporated or electroporated with control siRNA (Ci) or A20 siRNA (A20i) were stimulated with PMA/ionomycin (left panel) or anti-CD3/anti-CD28 (right panel) for 10 hours, after which the levels of IL-2 in the medium were analyzed. Panel C, Cleavage of A20 abolishes its NFκB-inhibiting potential. HEK293T cells were transfected with Bcl10 (upper panel) or API2-MALT1 (middle panel), and two different concentrations of A20-WT, A20-R439A, A20-p50, A20-p37 or the combination of A20-p50 and A20-p37. Twenty-four hours later, NFκB activation was measured. Data are shown as mean±s.d. (n=3).

FIG. 10: Inhibition of the proteolytic activity of (API2-)MALT1 decreases MALT1-mediated NFκB activation and IL-2 production. Panel A) NFκB activation in HEK293T cells transfected with API2-MALT1-WT or API2-MALT1-C464A. Panel B) IL-2 production (after 10 hours) and A20 cleavage (after 15, 30, or 60 minutes; 30 minutes MG132 pretreatment) in PMA/ionomycin treated Jurkat cells stably expressing MALT1-WT or MALT1-C464A. Data are shown as mean±s.d. (n=3).

Figure 11:
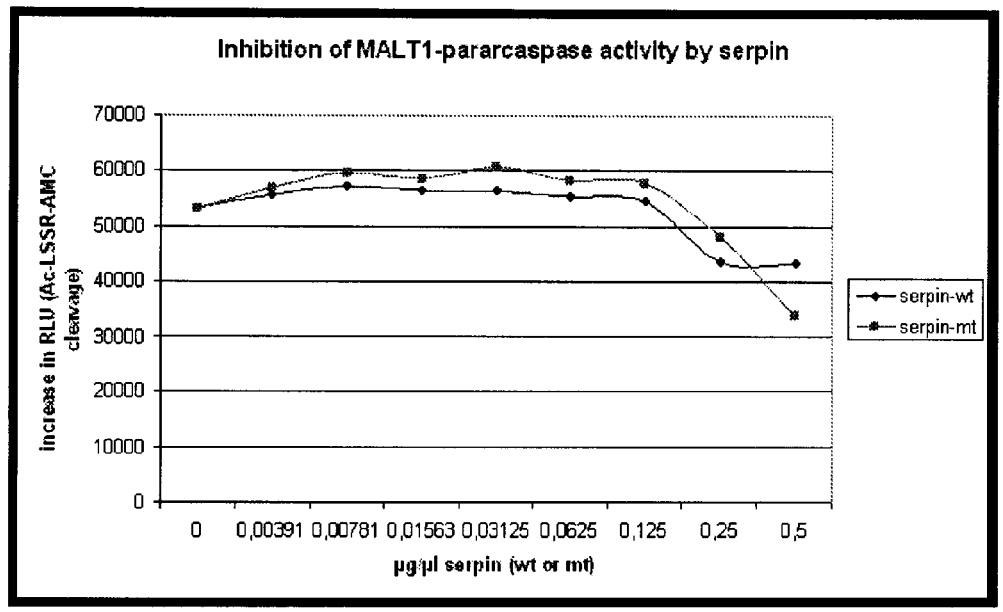

FIG. 11: Inhibition of the proteolytic activity of MALT1 by mutant and wild type *A. thaliana* serpin. *Arabidopsis thaliana* serpin (AT1g47710) is indicated as serpin-wt. In the mutant serpin (serpin-mt) the reactive center loop has been replaced by the sequence IKLA (SEQ ID NO:16) (Vercammen et al., 2006).

Figure 12:
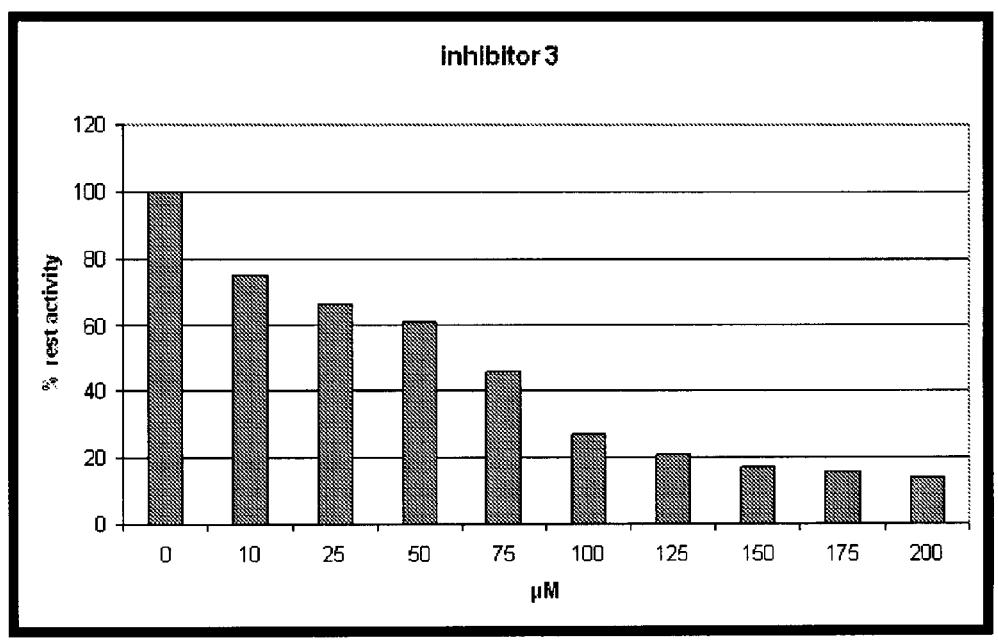

FIG. 12: Inhibition of the proteolytic activity of MALT1 by 5-{[5-(3-chloro-4-methylphenyl)-2-furyl]methylene}-2-thioxodihydro-4,6(1H,5H)-pyrimidinedione. Inhibitory effect of 5-{[5-(3-chloro-4-methylphenyl)-2-furyl]methylene}-2-thioxodihydro-4,6(1H,5H)-pyrimidinedione ("Inhibitor 3"; inh3 in Table 1) at different concentrations.

DETAILED DESCRIPTION OF THE INVENTION

Examples

Materials and Methods to the Examples
Antibodies, Plasmids and Other Reagents.

Antibodies used for immunodetection of the Flag epitope (M2) were from Sigma-Aldrich, for BCL10 (sc-5273), TRAF6 (sc-7221) and Lyn (44) from Santa Cruz Biotechnology, for anti-CD3 (clone UCHT-1) and anti-CD28 (clone 28.2) from Pharmingen and for phosphorylated IκB-α (Ser32/36, 5A5) and phosphorylated ERK (Thr202/Tyr204, #9101S) from Cell Signalling. Anti-β-actin (clone AC-15) was purchased from Sigma, anti-MALT1-C is a rabbit polyclonal antiserum raised against AA 731-824 of MALT1 (Baens et al., 2006). Anti-A20 (clone 59A624) was from eBioscience, anti-E-tag from Amersham Biosciences, anti-MALT1 (H-300) and anti-IκBα from Santa Cruz Biotechnology, anti-β actin from MP Biomedicals.

pCAGGS-E-hA20-R/A and pCAGGS-E-A20-RR/AA were constructed by PCR mutagenesis. Constructs encoding FLAG-Bcl10, Myc-MALT1 or Myc-MALT1-C/A and Myc-API2-MALT1 or Myc-API2-MALT1-C/A (fusion of exon 7 of API2 to exon 8 of MLT), were described previously (Noels et al., 2007). All other constructs for expressing proteins in eukaryotic cells were made in pcDNA3.1 encoding an N-terminal Flag-epitope (pcD-F-x, with x the gene of interest). To direct raft association of proteins, inserts were cloned in pcD-mp-F-x with the code for a myristoylation/palmytoylation (mp) motif of Lck (MGCVCSSNPEDD SEQ ID NO:3)) in front of the Flag epitope. A vector enabling expression of biotinylated proteins was constructed by introducing oligonucleotides encoding the Avi-tag sequence (GLNDIFEAQKIEWHE (SEQ ID NO:4)) (Beckett et al., 1999) downstream of the sequences for N-terminal Flag epitope in the plasmid pcDNA3.1 (pcD-F-bio-x). Two other vectors were generated encoding the bio-tag, preceded by a flexible linker (SGSSGSSG (SEQ ID NO:5)), C-terminal of the multiple cloning site (pcD-F-x-bioC and pcD-mp-F-x-bioC). These vectors were used to generate the different bio-constructs for MALT1 and mutants. MALT1 fragments with the LSSR (SEQ ID NO:1) mutation, at residues 146-149 generated by PCR-based mutagenesis, was subcloned in the (mp-)MALT1 construct. All other MALT1 mutants, pcD-F-IKKγ and pcD-HA-Ub (Ubiquitin) were constructed and described previously (Noels et al., 2007; Baens et al., 2006).

PMA was from Sigma, ionomycin and MG132 were from Calbiochem. siGENOME SMARTpool siRNA oligonucleotides against A20 and MALT1 as well as non-targeting siRNA were purchased from Dharmacon. Expression and purification of MALT1C-gyraseB has been described (Sun et al., 2004).

Cell Culture

HEK-293T and Jurkat T-cells were cultured in DMEM-F12 (Invitrogen) supplemented with 10% fetal calf serum at 37° C. in 5% $CO_2$. SSK41 MALT lymphoma B-cells) and—for the A20 experiments (example 6-9)—Jurkat T-cells were cultured in RPMI1640 (Invitrogen) supplemented with 10% fetal bovine serum, 2 mM glutamine, 0.4 mM sodiumpyruvate, 4 μM β-mercaptoethanol and antibiotics. Monoclonal stable cell lines were generated by electroporating $5 \times 10^6$ cells with 20 μg of linearized plasmid DNA (250 V, 960 μF, Genepulser BioRad), followed by single cell dilution and selection with the appropriate antibiotics. Monoclonal Jurkat cell lines were generated stably expressing BirA from a pMSCV-Flag-puromycin vector, alone or in combination with a bio-tagged version of MALT1, MALT1-R149A and MALT1-C464A and clones with equal expression levels were chosen for further experiments. To mimic antigen receptor stimulation, Jurkat T-cells were stimulated with 10 μg/ml anti-CD3/2.5 μg/ml anti-CD28 or 50 ng/ml PMA (Sigma-Aldrich) and 100 ng/ml ionomycin (Sigma-Aldrich) for the indicated time. After washing with PBS, cells were lysed for 30 min on ice in NDLB lysis buffer (0.3% NP-40, 20 mM Tris-Cl pH 7, 6, 110 mM NaCl, 2 mM EDTA and 10% glycerol, supplemented with phosphatase inhibitors (30 mM NaF, 1 mM $Na_3VO_4$, 2 mM $Na_2MoO_4$, 5 mM $Na_4P_2O_7$) and 1× Complete protease inhibitor cocktail (Roche Applied Science)). Jurkat cells overexpressing MALT1 or MALT1-C464A were described previously (Noels et al., 2007)

Primary human T-cells were purified from the blood of healthy volunteers (obtained from the Belgian Red Cross Blood Bank). Briefly, T-cells, B-cells and mononuclear cells were purified by Ficoll-Hypaque gradient centrifugation of buffy coat. T-cells were further purified by a nylon wool fiber column (Polysciences).

Transfection of Cells

HEK293T cells were transiently transfected by calcium phosphate DNA coprecipitation. Jurkat cells were transiently transfected with expression plasmids with the Amaxa Nucleofector kit according to the manufacturer's protocol (Amaxa AG). siRNA transfection of Jurkat cells was done by electroporation of 5×106 cells in 0.5 ml serum-free culture medium containing 400 nM siRNA oligos at 300 V and 1050 uF using a BioRad electroporator. After electroporation, cells were returned to 10 ml complete medium. Electroporation was repeated 24 h later and cells were maintained for 2 more days before stimulation and harvesting.

Gene Silencing, NFκB Reporter Assays and IL-2 Determination.

The following predesigned siRNAs were used for gene knock-down experiments in HEK-293T cells: a mix of AAG-GTACTGGAGCCTGAAGGA (SEQ ID NO:9) and AAGGT-TGCACAGTCACAGAAT (SEQ ID NO:10) for MALT1, a mix of AAGGGCTGGAAAATTGTTAGA (SEQ ID NO:11) and AAGGACTAAAATGTAGCAGTT (SEQ ID NO:12) for BCL10 and a control siRNA for GFP (Ambion). HEK-293T cells in 12-well plates were transfected with siRNA duplexes (50 nM) using Oligofectamine (Invitrogen). After 4 hours the medium was replaced and cells were transfected as described previously (Baens et al., 2006). NFκB reporter assays were performed as described (Baens et al., 2006; Heyninck et al., 1999). NFκB dependent luciferase expression and constitutive β-galactosidase expression are expressed as luc/bgal to normalize for potential differences in transfection efficiency.

siRNA transfection of Jurkat cells was performed by electroporation of 5 $10^6$ cells in 0.5 ml serum free medium containing 400 nM siRNAs (mix of 5'-CCTGTGAAATAG-TACTGCACTTACA (SEQ ID NO:13) and 5'-CACTCTGAAGTAAGAGCAATGGGAA (SEQ ID NO:14), Invitrogen) using a BioRad electroporator at 300V and 1050 μF. Electroporation was repeated 24 hours later and cells were cultured for 2 more days before harvesting. IL-2 in the supernatant of Jurkat cells, unstimulated or stimulated for 6 hours with 50 ng/ml PMA—100 ng/ml ionomcyin, was measured by ELISA according to the manufacturer's protocol (Pharmingen).

Bio-IPs and Western Blot Analysis

The bio-IP method is described by de Boer et al. (26). Briefly a protein of interest containing the biotinylation tag becomes biotinylated in vivo via co-expression of the E. coli BirA biotin protein ligase. After cell lysis in NDLB lysis buffer for 30 min on ice, the biotinylated protein complex is precipitated using paramagnetic streptavidin beads (Dynabeads M-280, Invitrogen) for 2 hours at 4° C., or IKKγ is precipitated with anti-Flag using protein-G sepharose beads (Ge Healthcare). Protein precipitates were washed four times in lysis buffer and boiled for 10 min at 95° C. in 1×SDS gel loading buffer (final concentration of 4% SDS and 300 mM β-mercaptoethanol). All samples were fractionated on 4-12% SDS-polyacrylamide gels (NuPage, Invitrogen) and transferred to polyvinylidene difluoride membranes (GE Healthcare-Life Sciences) for detection.

For the A20 experiments (example 6-9), for co-immunoprecipitation 1.5×$10^7$ Jurkat cells were lysed in 1 ml lysis buffer (20 mM Tris pH 7.5, 137 mM NaCl, 1.5 mM MgCl2, 1% Tx-100 and phosphatase and protease inhibitors). Immunoprecipitation of MALT1 was done by adding 8 μg anti-MALT1 and overnight incubation at 4°, followed by the addition of Protein A Trisacryl beads (Pierce) for 2 hours. Beads were washed four times with lysis buffer and eluted by adding Laemmli loading buffer.

Coprecipitating proteins were separated by SDS-PAGE and analyzed by Western blotting using ECL detection (PerkinElmer Life Sciences). For detection of A20 cleavage, Jurkat cells were stimulated with 10 μg/ml anti-CD3/10 μg/ml anti-CD28 or with 200 ng/ml PMA/1 μM ionomycin for the indicated times. Cells were lysed in 100 μl lysis buffer and 60 μg lysate was analyzed by Western blotting with anti-A20 antibody.

Paracaspase Assay, Substrate and Inhibitor.

Assays were performed in 50 μl with 100 μM substrate in a buffer consisting of 50 mM MES (pH 5.5), 150 mM NaCl, 10% (w/v) sucrose, 0.1% (w/v) CHAPS, 10 mM dithiothreitol and 1 M (NH4)3citrate, supplemented with bio-IP purified MALT1 or mutants, isolated from 3 $10^6$ transiently transfected HEK-293T cells, or with 1 μg recombinant MALT1 or MALT1-C464A (Sun et al., 2004). Time-dependent release of free amido-4-methylcoumarin (AMC) was measured on a FLUOstar Galaxy reader (BMG Labtechnologies, Offenburg, Germany), and activity was expressed as the increase of RLU per minute per well. Ac-LSSR-AMC (see SEQ ID NO:1), Z-LSSR-CHO (see SEQ ID NO:1) and Ac-GASR-CHO (see SEQ ID NO:2) were purchased from Anaspec. Compounds used in the screening were obtained from ChemBridge.

In Vitro Cleavage of A20.

The expression vector pLT10T3A20 containing the human A20 gene under the control of a T7 promoter was used for in vitro coupled transcription-translation of [35S]methionine labeled human A20 in an in vitro reticulocyte lysate system (Promega Biotec) according to the manufacturers protocol. Translation reactions (2 μl) were incubated with 500, 1000 or 1500 nM of recombinant MALT1C-gyraseB (Sun et al., 2004) in a total volume of 50 μl paracaspase assay buffer (50 mM MES pH 5.5, 150 mM NaCl, 10% sucrose w/v, 0.1% w/v CHAPS, 10 mM DTT, 1 M ammonium citrate) for 1.5 hours at 37° C. The resulting cleavage products were analyzed by SDS-PAGE and autoradiography.

Example 1

The MALT1 p20 Domain has Auto-Proteolytic Activity

The MALT1 protein synergistically activates NFκB with BCL10 when co-expressed in 293T cells. Human MALT1 contains a caspase p20-like domain. Interestingly, mutation of the putative catalytic cysteine (C464A) in this domain reduced the synergism with BCL10 (Lucas et al., 2001 and FIG. 1, Panel A), hypothesizing that BCL10-mediated dimerization of MALT1 might initiate NFκB signaling via activation of its caspase p20-like domain.

Figure 1:
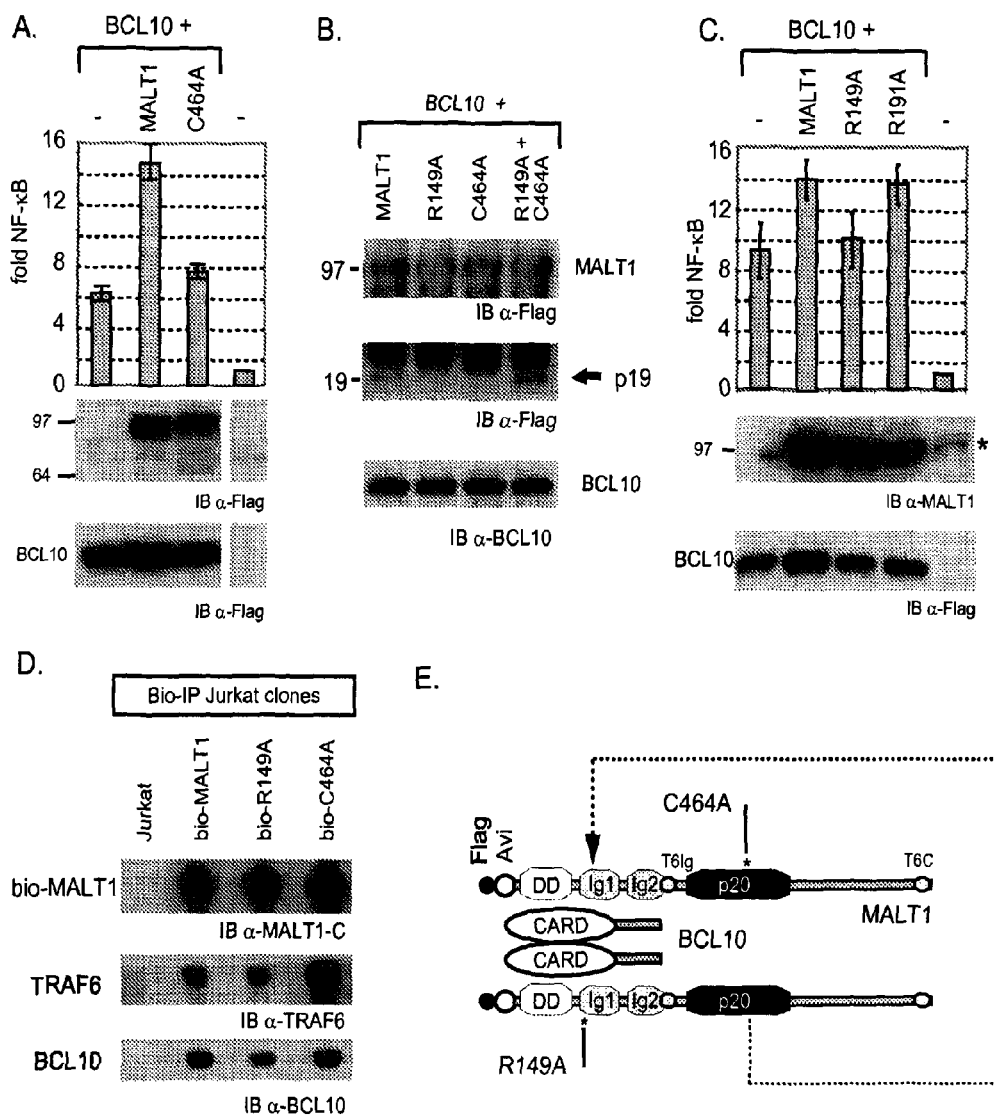
FIG. 1: BCL10 mediates intermolecular auto-proteolytic cleavage of MALT1 at R149. Panel A) MALT1 proteolytic activity and Panel C) MALT1 proteolysis at R149 are required to synergistically activate NFκB with BCL10 in HEK293T cells. NFκB-reporter assays of HEK293T cells transiently expressing BCL10, MALT1 and indicated mutants. NFκB-dependent luciferase activity is shown as fold induction of vector-transfected cells and represents the mean+/−S.D. of at least three independent experiments. Immunoblot with anti-Flag and anti-MALT1-C confirms equal level of expression. *endogenous MALT1. Panel B) immunoblot analysis of streptavidin pull-downs (Bio-IP) of MALT1 and its mutants co-expressed with BCL10 in HEK293T cells. Arrow indicates the N-terminal cleavage fragment of 19 kDa (p19). All molecular mass standards are in kDa. Panel D) The R149A and the C464A mutation do not disrupt the interaction of MALT1 with BCL10 and TRAF6, assessed via immunoblots of bio-IPs from Jurkat cells with stable expression of MALT1 or the R149A and C464A mutants. Panel E) Mechanism of BCL10-mediated intermolecular auto-proteolytic cleavage of MALT1. Flag: Flag epitope, Ig: immunoglobulin-like domain, p20: caspase p20-like domain, T6-Ig/T6-C: TRAF6 binding site in the second Ig domain and the C-terminus, Avi: Avi-tag for streptavidin-mediated pull-down or bio-IP, CARD: caspase recruitment domain.

To investigate whether BCL10-mediated dimerization of MALT1 induces its auto-proteolysis, we performed streptavidin-mediated pull-downs of MALT1 with an N-terminal tag. Western blot analysis indeed showed the presence of an N-terminal fragment of 19 kDa (p19), which was absent without BCL10 co-expression or when BCL10 was co-expressed with the C464A MALT1 mutant (FIG. 1, Panel B).

Metacaspases have specificity towards R/K residues in the substrate P1 position (Vercammen et al., 2004). Based on the apparent molecular weight of the N-terminal fragment, R/K residues in the first Ig-like domain of MALT1 were mutated to evaluate their possible involvement in the cleavage site leading to the generation of p19. Introduction of an R149A mutation in MALT1 prevented both p19 production upon BCL10 co-expression (FIG. 1, Panel B) and loss of synergism with BCL10 for NFκB activation, whereas MALT1-R191A behaved like wild-type MALT1 (FIG. 1, Panel C). Co-IP experiments showed that both the C464A and R149A mutants are still able to interact with BCL10 (FIG. 1, Panel D). These data suggest the hypothesis that the synergism of MALT1 for BCL10-induced NFκB activation requires its auto-proteolysis at R149.

Auto-proteolytic cleavage of initiator caspases upon proximity-driven dimerization occurs via interchain cleavage. To investigate whether MALT1 processing might result from an intermolecular, auto-proteolytic cleavage event we co-expressed BCL10 together with the R149A and the C464A mutants of MALT1. FIG. 1, Panel B shows the reappearance of the p19 fragment, absent when each of the MALT1 mutants was co-expressed with BCL10 separately. Taken together the data suggest that MALT1 has interchain auto-proteolytic activity, with C464 involved in the catalytic site and R149 in the cleavage site (FIG. 1, Panel E).

Example 2

Raft Association of MALT1 is Sufficient for Cleavage into p19 and p76 Fragments

Figure 2:
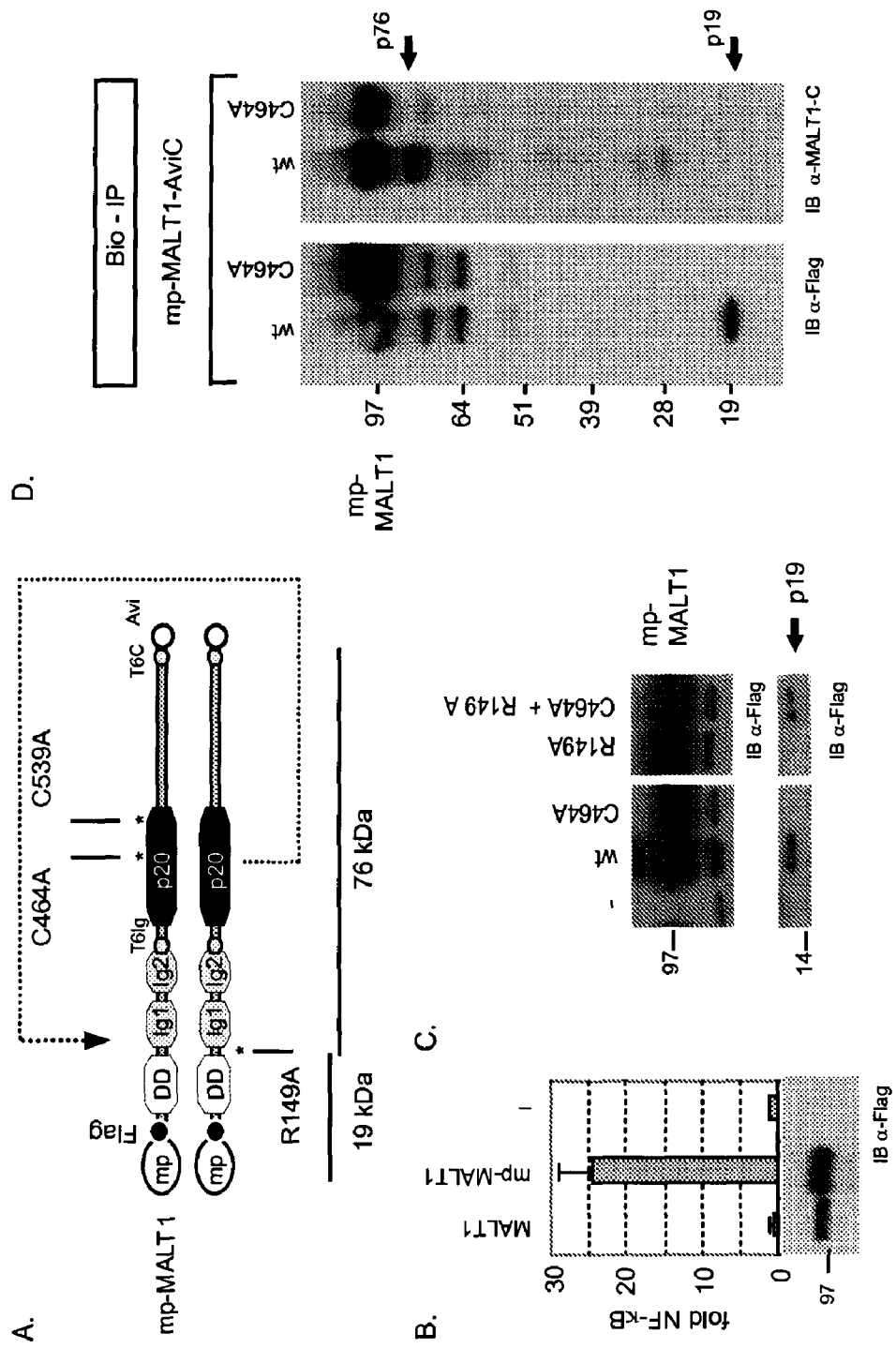
FIG. 2: Raft association of MALT1 induces auto-proteolytic cleavage at R149. Panel A) Mechanism of auto-proteolytic interchain cleavage of mp-MALT1. mp: myristoylation-palmitoylation sequence. Panel B) NFκB-reporter assays of HEK293T cells transiently expressing MALT1, mp-MALT1 or empty vector. NFκB-dependent luciferase activity is shown as fold induction of vector-transfected cells and represents the mean+/−S.D. of at least three independent experiments. Panel C) immunoblot analysis of mp-MALT1 and mutants expressed transiently in HEK293T cells. Panel D) immunoblot analysis of mp-MALT1 bio-IPs from HEK293T cells. The N- and C-terminal cleavage fragments of 19 and 76 kDa respectively are indicated. All molecular mass standards are in kDa.

Previously we demonstrated that BCL10 co-expression induced the redistribution of MALT1 to the lipid rafts in 293T cells (Noels et al., 2007). We induced raft association of MALT1 in 293T cells by adding a myristoylation-palmitoylation signal sequence (mp-MALT1). This was sufficient to activate an NFκB luciferase reporter gene and to generate the p19 fragment, whereas ectopic expression of MALT1 was not able to do so (FIG. 2, Panel B). Western blot analysis of detergent resistant membrane fractions confirmed the association of mp-MALT1 with the lipid rafts, in contrast to MALT1 shown previously to reside exclusively in cytosolic fractions (Noels et al., 2007; Baens et al., 2006), and the p19 fragment was detected in raft fractions) as well as in total cell lysates (FIG. 2, Panel C). Again no p19 was detected upon expression of either R149A- or C464A-mp-MALT1, whereas their co-expression restored p19 formation (FIG. 2, Panel C).

To identify C-terminal fragments resulting from MALT1 proteolysis, we performed bio-IPs with mp-MALT1 constructs carrying a C-terminal Avi-tag. A 76 kDa fragment (p76) could be visualized which was absent in pull-downs from the C464A mutant of mp-MALT1 (FIG. 2, Panel D). Since MALT1 has a molecular weight of approximately 96 kDa, this is consistent with the cleavage of MALT1 in p19 and p76 fragments.

Example 3

MALT1 Paracaspase Shows In Vitro Proteolytic Activity

Caspases efficiently cleave synthetic substrates consisting of a four amino acid recognition sequence linked, via the carboxy-terminal aspartate, to a fluorogenic amine. Based on the presumed cleavage site of MALT1, Ac-LCCR-AMC (see SEQ ID NO:15) would be a suitable substrate for demonstrating MALT1 paracaspase activity in vitro. As the synthesis of a LCCR (SEQ ID NO:15) peptide is difficult, we first demonstrated that mutating both C147 and C148 in MALT1 to S, resulted in a LSSR (SEQ ID NO:1) MALT1 mutant that could still be cleaved in cellular assays (FIG. 3, Panel A). Next we showed that bio-IP purified MALT1 was indeed able to cleave Ac-LSSR-AMC (see SEQ ID NO:1) in vitro, whereas bio-1P purified C464 mutant was not (FIG. 3, Panel B). Bio-IP of mock-transfected cells also showed no activity, which together with the results for bio-IP-purified C464A MALT1 excludes precipitation of a contaminating protease. Interestingly the proteolytic activity was dependent on the addition of the cosmotropic salt ammonium citrate, as previously shown for caspases (Boatright et al., 2003). Substrate cleavage by MALT1 was efficiently blocked by a Z-LSSR-CHO (see SEQ ID NO:1) and a Z-GASR-CHO (see SEQ ID NO:2) inhibitor at equimolar concentrations (FIG. 3, Panel B). Furthermore, the R149A mutant was as efficient in substrate processing as MALT1 (FIG. 3, Panel C). Finally, the recombinant MALT1 p20 fragment (Sun et al., 2004) efficiently cleaved the Ac-LSSR-AMC (see SEQ ID NO:1) substrate, whereas the recombinant C464A mutant failed to do so, although its higher concentration (FIG. 1, Panel D). Again, adding Z-LSSR-CHO (see SEQ ID NO:1) or Z-GASR-CHO (see SEQ ID NO:2) completely blocked the proteolytic activity of recombinant MALT1. Taken together the data indicate that MALT1 has proteolytic activity in vitro and that this activity is dependent on the presence of C464 but independent of R149.

Example 4

Role for MALT1 Auto-Proteolysis in NFκB Activation

To further assess the possible role of MALT1 auto-proteolysis for NFκB signaling, we generated Jurkat cell lines with stable expression of MALT1 and its R149A and C464A mutants respectively. Ectopic expression of MALT1 in Jurkat cells increased phosphorylation of IκBα in response to PMA/ionomycin or CD3/CD28 stimulation compared to equal levels of the R149A- or C464A-MALT1 mutant (FIG. 4, Panels A and B). Activation and phosphorylation of ERK in response to PMA/ionomycin or CD3/CD28 stimulation is MALT1-independent (Ruland et al., 2003) and was unaffected (FIG. 4, Panels A and B). Likewise, Jurkat cells pre-treated with siRNAs against MALT1 showed reduced phosphorylation of IκBα after PMA/ionomycin treatment. This reduction could be reversed by ectopic expression of MALT (insensitive to the siRNA) but not by the R149A or C464A mutants (FIG. 4, Panel C). Finally, overexpression of MALT1 enhanced NFκB-dependent production of IL2 after stimulation with PMA/ionomycin more potently than either the R149A or the C464A mutant (FIG. 4, Panel D), consistent with the higher NFκB activation by wild-type MALT1. Taken together, these data indicate that intermolecular auto-proteolytic cleavage of MALT1 is involved in its NFκB activating potential.

Example 5

The p76 Fragment of MALT1 Activates NFκB Signaling

Thus far, our data indicate that auto-proteolytic cleavage of MALT1 at R149 is involved in its NFκB signaling potential. To study the properties of the MALT1 cleavage fragments, we generated expression constructs for p19, p76 and MALT1-C (FIG. 5, Panel A). The latter fragment activated the BCL10-IKK pathway in vitro via oligomerization and activation of TRAF6 (Sun et al., 2004). Similar to ectopic expression of MALT1, transient expression of MALT1-C did not activate an NFκB reporter gene in 293T cells (FIG. 5, Panel B), nor did the p19 construct (data not shown). Expression of the p76 fragment however potently induced NFκB activity, suggesting that removal of the N-terminal DD releases NFκB signaling potential of MALT1 (FIG. 5, Panel B).

NFκB activation by MALT1 requires TRAF6 binding via two distinct sites (19), which are both present in the p76 cleavage fragment. Mutation of one TRAF6 binding site, either E313A/E316A (T6Ig-m) or E806A (T6C-m), abolished the potential of p76 to activate NFκB signaling in 293T cells (FIG. 5, Panel B). Bio-IP experiments showed that p76, like MALT1 interacted with TRAF6, whereas both the T6Ig-m and the T6C-m mutation potently reduced this interaction, though a complete block of TRAF6 binding required mutation of both sites (T6Ig/C-m) (FIG. 5, Panel B). In contrast, the MALT1-C fragment still bound TRAF6 via the T6C binding site, however did not activate NFκB signaling by its own. Furthermore, NFκB activation by p76 in 293T cells was associated with increased polyubiquitination of IKKγ (FIG. 5, Panel C). Taken together, these data suggest that MALT1 p76, which can be formed by auto-proteolysis, activates NFκB in a TRAF6-dependent manner.

The interaction of MALT1 with BCL10 requires both the DD and the Ig-like domains of MALT1 (Noels et al., 2007), suggesting that BCL10 no longer interacts with or is required for NFκB activation by p76. Bio-IPs for p76 indeed failed to demonstrate an interaction with BCL10 (FIG. 5, Panel B), conform our previous results with a MALT1 construct lacking the DD domain (Noels et al., 2007). Moreover, siRNA-mediated knock-down of BCL10 expression did not affect NFκB activation by p76 (FIG. 5, Panel D). In contrast, reducing the levels of endogenous MALT1 enhanced p76-mediated NFκB activation (FIG. 5, Panel D), most likely because of an increase of free TRAF6 otherwise bound to MALT1. Taken together, these data suggest that NFκB activation by the p76 cleavage fragment of MALT1 no longer requires BCL10.

Example 6

T Cell Receptor Stimulation Results in A20 Cleavage

The zinc finger protein A20 negatively regulates proinflammatory gene expression by down-regulating NFκB activation in response to different stimuli (Beyaert et al., 2000; Lee et al, 2000). Most cell types do not constitutively express A20 but rapidly up-regulate A20 mRNA expression upon stimulation of NFκB, implicating A20 in the negative feedback regulation of NFκB activation (Beyaert et al., 2000). In contrast, lymphoid organs and especially T-lymphocytes have been reported to constitutively express A20 mRNA (Lee et al., 2000; Tewari et al., 1995). In accordance with these data, we observed constitutive protein expression of A20 in Jurkat T-cells (FIG. 6, Panel a), suggesting a potential role for posttranslational regulation of A20 in these cells. Interestingly, triggering the TCR complex of these cells with agonistic anti-CD3/anti-CD28 antibodies led to a rapid decline in A20 expression upon stimulation for 15 to 30 minutes (FIG. 6, Panel a, upper panel). Expression levels of A20 returned to baseline levels 60 minutes after stimulation. This is similar to the rapid degradation and resynthesis of IκBα that is indicative of NFκB activation.

Interestingly, longer exposure of the same immunoblot revealed the rapid appearance of a faint protein band of approximately 37 kDa that was specifically recognized by the anti-A20 antibody (FIG. 6, Panel a). The latter is a mouse monoclonal antibody that recognizes the C-terminal zinc finger containing part of A20, indicating that the 37 kDa band represents a C-terminal protein fragment of A20 (which we will further refer to as A20p37). Similar results were obtained after administration of PMA/ionomycin, which mimics TCR signaling by activating PKCθ (FIG. 6, Panel b). Since A20p37 was already detectable 15 minutes after TCR stimulation and its production could not be blocked by pre-treating the cells with the protein translation inhibitor cycloheximide, a posttranslational proteolytic event rather than de novo protein synthesis seems to generate A20p37.

Because the A20p37 levels were rather low, we speculated that this fragment of A20 was unstable and rapidly degraded. Indeed, treatment of Jurkat cells with either anti-CD3/anti-CD28 or PMA/ionomycin together with the proteasome inhibitor MG132 resulted in the accumulation of A20p37 (FIG. 6, Panel c), indicating that the A20p37 fragment is rapidly degraded by the proteasome. Importantly, TCR stimulation not only stimulated the production of A20p37 in Jurkat cells but also in primary human T-cells (FIG. 6, Panel d). As both TCR- and PMA/ionomycin-induced signaling pathways converge on PKCθ activation (Sun et al., 2000), resulting in the assembly of the CBM complex 1, (Ruland et al., 2001, 2003; Ruefli-Brasse et al., 2003; Wang et al., 2002; Su et al., 2002) our observations suggest that the CBM complex may be involved in the generation of A20p37. Gene disruption studies have shown that the CBM complex is not only indispensable for TCR-induced NFκB activation but also mediates BCR-induced signaling (Sommer et al., 2005; Ruland et al., 2001; Ruefli-Brasse et al., 2003; Su et al., 2002; Egawa et al., 2003). Therefore, we investigated whether A20p37 was also generated upon activation of the B-cell lymphoma cell lines Raji and SSK41. In both cell lines PMA/ionomycin stimulation resulted in production of A20p37, which accumulated upon proteasome inhibition with MG132 (FIG. 6, Panel e). Moreover, A20p37 was also generated upon stimulation of SSK41 cells with anti-IgM, which triggers the BCR itself (FIG. 6, Panel e). The latter cells are derived from a MALT-type B-cell lymphoma and over express MALT1 because of nine copies of the MLT gene in their genome (Sanchez-Izquidero et al., 2003).

Interestingly, in SSK41 cells but not Raji cells, treatment with MG132 as such was sufficient for generating A20p37, suggesting that overexpression of MALT1 in SSK41 cells not only spontaneously induces NFκB activation but also the specific proteolytic cleavage of A20 (Sanchez-Izquidero et al., 2003 and FIG. 6, Panel e). Finally, it should be noted that stimulation of Jurkat cells with TNF, which does not lead to activation of the CBM complex, did not induce the generation of A20p37.

Example 7

A20 Cleavage is Mediated by MALT1

Altogether, the above data suggest a role for the CBM complex, and for MALT1 in particular, in the generation of A20p37 after BCR- and TCR-stimulation. In order to further analyze the role of MALT1 in TCR-induced A20p37 production, we transfected Jurkat cells with an siRNA specifically directed against MALT1 (siMALT1) and stimulated the cells with anti-CD3/anti-CD28 in the absence or presence of MG132. As shown by Western blotting, siMALT1 efficiently down-regulated MALT1 expression. Interestingly, in contrast to non-transfected or control siRNA transfected cells, siMALT1 treated cells did not show detectable levels of A20p37 after TCR-triggering, even in the presence of MG132 (FIG. 7, Panel a). Comparable results were obtained with a different set of MALT1 targeting siRNA molecules. As this siRNA experiment further points to a role of MALT1 in the proteolytic generation of A20p37 upon TCR-triggering, we next wanted to investigate whether MALT1 and A20 reside within one complex in TCR stimulated cells. For this purpose, Jurkat cells were stimulated for different time periods with anti-CD3/anti-CD28 and MALT1 immunoprecipitates were analyzed for the presence of Bcl10 and A20 by immunoblotting. Whereas Bcl10 already coimmunoprecipitated with MALT1 in unstimulated cells, A20 did not (FIG. 7, Panel b). However, 10 minutes TCR-stimulation allowed A20 to enter the Bcl10/MALT1 complex, and this interaction lasted for at least 60 minutes (FIG. 7, Panel b). Similarly, also PMA/ionomycin treatment led to the recruitment of A20 into the Bcl10/MALT1 complex (FIG. 2, Panel B, last lane). Our observation that MALT1 and A20 reside in a single complex upon TCR stimulation suggests that MALT1 might be responsible for the TCR-induced proteolytic generation of A20p37. Although MALT1 contains a C-terminal domain that shows strong homology to the catalytic domain of caspases (Uren et al., 2000; Snipas et al., 2004), no proteolytic activity of MALT1 could be demonstrated so far. Based on sequence homology with caspases, MALT1 cysteine residue 464 was predicted as part of the catalytic site. To analyze the potential of MALT1 to generate the p37 fragment of A20, we tested the ability of MALT1 or its catalytically inactive C464A mutant to induce the cleavage of N-terminally E-tagged A20 upon overexpression in HEK293T cells. Bcl10 was cotransfected in order to activate MALT113. Western blotting and immunodetection with the anti-A20 antibody revealed that overexpression of Bcl10/MALT1 induces a 37 kDa fragment of A20 that corresponds in size to A20p37 that was observed in Jurkat cells stimulated with PMA/ionomycin (FIG. 7, Panel c, left panel). In addition, immunodetection of the same western blot with an anti-E-tag antibody revealed a protein fragment of approximately 50 kDa upon overexpression of Bcl10/MALT1 (referred to as A20p50, FIG. 7, Panel c, right panel). Since A20 has a molecular weight of approximately 85 kDa, these findings indicate that A20 is cleaved at a single site, resulting in an N-terminal fragment of 50 kDa (A20p50) and a C-terminal part of 37 kDa (A20p37). Strikingly, co-expression of Bcl10/MALT1-C464A did not generate any of these A20 fragments, indicating that the observed cleavage of A20 depends on the proteolytic activity of MALT1 (FIG. 7, Panel c). Consistent with the above results obtained upon overexpression of Bcl-10/MALT1, also overexpression of the MALT lymphoma associated fusion protein API2-MALT1 resulted in the proteolysis of A20 into a p50 and a p37 fragment. Moreover, the catalytically inactive API2-MALT1-C464A mutant failed to cleave A20 (FIG. 7, Panel c).

Both in case of API2-MALT1 as well as Bcl10/MALT1 overexpression, the A20p37 C-terminal fragment was relatively less prominent than the N-terminal A20p50 fragment (FIG. 7, Panel c), which is in line with the rapid degradation of A20p37 observed in T-cells and B-cells.

The proteolytic activity of MALT1 on A20 was subsequently confirmed in an in vitro assay with recombinant MALT1 and [$^{35}$S]methionine-labeled A20. The recombinant MALT1 we used represents the C-terminal caspase-like domain containing part of MALT1 (residues 334-824) fused to a fragment of bacterial gyrase B (MALT1C-gyraseB), which enables MALT1-C oligomerization. This MALT1 fusion has previously already been shown to activate the IKK-complex in an in vitro kinase assay (Sun et al., 2004). In vitro incubation of radiolabeled A20 with recombinant MALT1C-gyraseB resulted in the generation of an A20 fragment of approximately 50 kDa (FIG. 7, Panel d), which corresponds in size to the N-terminal fragment of A20 that was detected in Bcl-10/MALT1 and API2-MALT1 transfected HEK293T cells (FIG. 7, Panel c). In contrast, incubation of A20 with the catalytically inactive MALT1C-gyraseB-C464A mutant protein did not result in A20 cleavage. We were unable to detect the C-terminal A20p37 fragment in the in vitro assay. The latter most likely reflects the lower stability of this fragment as already mentioned above, as well as the fact that the A20p37 fragment contains 3 times less radiolabeled methionine residues than the N-terminal A20 fragment, decreasing the sensitivity of detection. Altogether these data indicate that MALT1 is a functional cysteine protease that is able to cleave A20.

Example 8

Arginine-Specific Cleavage by MALT1

In caspases, P1 specificity directed to aspartic acid is dictated by arginine and glutamine residues located in the p20 and p10 caspase subunits, respectively, which help to position the substrate aspartic acid in the catalytic site (Earnshaw et al., 1999). Although paracaspases such as MALT1 are caspase-like proteins, alignment of paracaspases, mammalian caspases and plant metacaspases (another family member of the CD clan of proteases with a caspase-like domain) shows that the above mentioned glutamine is replaced by an aspartic acid residue in case of paracaspases and metacaspases (Uren et al., 2000). This predicts a basic substrate-specificity for paracaspases and metacaspases. Indeed, a P1 arginine-specific substrate cleavage has recently been demonstrated for several plant metacaspases (Vercammen et al., 2004). This led us to evaluate the role of specific arginine residues in the MALT1-mediated cleavage of A20. A20 consists of an N-terminal OTU domain and a C-terminal domain containing 7 zinc finger structures (Wertz et al. 2004). Based on the molecular weights of the N-terminal p50 and C-terminal p37 proteolytic fragments of A20 that were generated by MALT1, A20 cleavage was predicted to take place between its first and second zinc finger (FIG. 8, Panel a). Within this linker region, three arginine residues can be found. In order to evaluate the potential cleavage of A20 at these sites, we generated a first A20 mutant in which both arginine 410 and 411 were mutated to alanine (A20-R410/411A), as well as a second A20 mutant in which arginine 439 was mutated to alanine (A20-R439A) (FIG. 8, Panel a). We next investigated if these A20 mutants could still be processed by MALT1 upon co-expression with MALT1/Bcl10 in HEK293T cells. Bcl10/MALT1-mediated processing of wild-type A20 or A20-R410/411A was similar (FIG. 8, Panel b). In contrast, we could not detect any Bcl10/MALT1-mediated processing of the A20-R439A mutant. Similar data were obtained when the A20 mutants were co-expressed with API2-MALT1 (FIG. 8, Panel c). These results indicate that MALT1-mediated processing of A20 occurs at R439 in the linker region between the first and the second zinc finger, thereby physically separating its N-terminal OTU domain and C-terminal zinc finger domain.

Example 9

MALT1 Inhibits the NFκB Inhibitory Function of A20

We next wanted to investigate the functional consequences of MALT1-mediated processing of the NFκB inhibitor A20. Knockout as well as overexpression studies have shown that A20 functions as a negative regulator of NFκB activation in response to multiple stimuli (Beyaert et al., 2000; Lee et al., 2000; Boone et al., 2004) but an inhibitory function in TCR-induced signaling has to our knowledge not yet been described. Therefore, we first investigated whether A20 overexpression inhibits the NFκB dependent expression of a luciferase reporter gene in response to Bcl10 or API2-MALT1 overexpression in HEK293T cells. Indeed, overexpression of A20 dose-dependently inhibited NFκB activation induced by over-expression of Bcl10 or API2-MALT1 (FIG. 9, Panel A). The inhibitory function of A20 on MALT1 signaling was further confirmed by siRNA-mediated knockdown of A20 expression in Jurkat cells, after which the effect on TCR-induced expression of the NFκB-dependent IL-2 gene was investigated. Compared to control-siRNA (Ci) transfected cells, cells transfected with A20-siRNA (Ai) produced significantly higher amounts of IL-2 in response to stimulation with anti-CD3/anti-CD28 or PMA/ionomycin (FIG. 9, Panel B).

Identical results were obtained with another set of siRNA molecules targeting A20. As these results establish A20 as a negative regulator of NFκB activation in response to TCR signaling, we went on to evaluate the effect of MALT1-mediated cleavage of A20 on its NFκB inhibitory function. We first compared the effect of overexpression of respectively wild type A20 and the non-cleavable A20-R439A mutant on Bcl10, API2-MALT1 and PMA induced NFκB activation in HEK293T cells. A20-R439A still inhibited NFκB activation in response to all these stimuli, and was even slightly more effective than wild-type A20 (FIG. 9, Panel C). These results indicate that A20 cleavage is not required for its NFκB inhibitory function but rather could lead to its inactivation.

To further investigate the latter assumption, we also analyzed the NFκB inhibiting potential of the individual A20p50 and A20p37 fragments that result from MALT1-mediated processing of A20. In contrast to full length A20, overexpression of the N-terminal A20p50 fragment had no inhibitory effect on Bcl10, API2-MALT1 and PMA induced NFκB activation (FIG. 9, Panel C). The C-terminal A20p37 fragment still inhibited NFκB activation, although much less efficient than full length A20. Although this suggests that MALT1-mediated processing of A20 diminishes its NFκB inhibitory function, we wanted to evaluate a possible synergistic NFκB inhibitory effect of the p50 and p37 fragments of A20. When we co-expressed both fragments and analyzed their joined NFκB inhibitory potential, we could not detect any contribution of the N-terminal fragment to the NFκB inhibiting effect of A20p37 (FIG. 9, Panel C). These results, as well as our observation that the endogenous A20p37 fragment is rapidly degraded after its generation, let us to conclude that MALT1-mediated processing of A20 considerably compromises its NFκB inhibitory function.

Previous data have shown that a proteolytically inactive MALT1-C464A mutant can still activate IκB kinases in an in vitro reconstitution experiment (Sun et al., 2004), indicating that the proteolytic activity of MALT1 is not essential for MALT1-induced NFκB activation. However, taking into account our finding that MALT1 proteolytically inactivates an NFκB inhibitory protein, one would expect a more quantitative difference between wild type MALT1 and MALT1-C464A induced NFκB activation. Indeed, less efficient NFκB activation by the catalytically inactive MALT1 mutant was previously already reported by others (Uren et al., 2000; Lucas et al., 2001). To confirm these data, we first compared the potential of API2-MALT1 or API2-MALT1-C464A overexpression to activate the expression of an NFκB dependent luciferase reporter gene in Jurkat cells. Whereas both API2-MALT1 and API2-MALT1-C464A were able to activate NFκB, the response was much lower upon overexpression of the proteolytically inactive API2/MALT1 mutant (FIG. 10, Panel A), which is consistent with the absence of A20 cleavage in the latter case. Similarly, stable overexpression of wild type MALT1 enhanced the NFκB dependent expression of IL-2 in response to PMA/ionomycin much more potently than overexpression of MALT1-C464A, consistent with the specific cleavage of A20 and the higher NFκB activation by wild type MALT1 (FIG. 10, Panel B).

Example 10

Inhibition of the MALT1 Proteolytic Activity by *A. thaliana* Serpin

Based on the similarity of the MALT1 proteolytic action and that of plant metacaspases (Vercammen et al., 2004) the possible inhibitory action of *A. thaliana* serpin (AT1g47710) and its IKLA-mutant (SEQ ID NO:16) form (Vercammen et al. 2006) was evaluated in the paracaspase assay, as described in materials and methods to the examples. The results are summarized in FIG. 11. Inhibition of the MALT1 paracaspase activity is possible, but only at relatively high concentrations of serpin. Surprisingly, the IKLA-mutant (SEQ ID NO:16), which is inactive versus plant metacaspase (Vercammen et al., 2006) is performing better than wild type serpin at higher concentrations.

Example 11

Screening of Small Compound Inhibitors Using the Malt Paracaspase Assay

The malt paracaspase assay as described in this invention can easily be used for high throughput screening of malt paracaspase inhibitors. A set of 27 compounds, selected from the ChemBridge library (Table 1) was used in a first screening. One compound showed significant concentration dependent inhibition of the malt paracaspase activity (FIG. 12).

TABLE 1

Chemical compounds used in the screening for inhibitors of the malt paracaspase activity.

| Structure | Chem-Bridge ID | PSB ID | Properties | MolName |
|---|---|---|---|---|
| $C_{21}H_{22}N_4O_2S$ | 5108668 | Inh01 | Mol Weight: 394<br>cLogP: 2.94<br>LogSW: −4.59<br>RB: 6<br>tPSA: 79.4<br>hDon: 2<br>hAcc: 4 | ethyl 2-benzyl-3-[(3-thioxo-3,4-dihydro-2-quinoxalinyl)-hydrazono]butanoate |
| $C_{17}H_{13}Cl_3N_2OS_2$ | 5157732 | Inh02 | Mol Weight: 432<br>cLogP: 5.38<br>LogSW: −6.94<br>RB: 5<br>tPSA: 42.0<br>hDon: 1<br>hAcc: 2 | N-[1-(1,3-benzothiazol-2-ylthio)-2,2,2-trichloroethyl]-2-phenylacetamide |
| $C_{16}H_{11}ClN_2O_3S$ | 5376346 | Inh03 | Mol Weight: 347<br>cLogP: 4.58<br>LogSW: −5.64<br>RB: 2<br>tPSA: 71.3<br>hDon: 2<br>hAcc: 3 | 5-{[5-(3-chloro-4-methylphenyl)-2-furyl]methylene}-2-thioxodihydro-4,6(1H,5H)-pyrimidinedione |
| $C_{17}H_{15}N_3S$ | 5406426 | Inh04 | Mol Weight: 293<br>cLogP: 5.28<br>LogSW: −5.85<br>RB: 4<br>tPSA: 37.3<br>hDon: 1<br>hAcc: 2 | 4-methyl-benzaldehyde (4-phenyl-1,3-thiazol-2-yl)-hydrazone |
| $C_{17}H_{12}N_2O_3S$ | 5526826 | Inh05 | Mol Weight: 324<br>cLogP: 3.35<br>LogSW: −3.85<br>RB: 2<br>tPSA: 69.6<br>hDon: 2<br>hAcc: 3 | 5-(4-hydroxybenzyl-idene)-1-phenyl-2-thioxodihydro-4,6(1H,5H)-pyrimidinedione |
| $C_{18}H_{17}N_5$ | 5625954 | Inh06 | Mol Weight: 303<br>cLogP: 4.19<br>LogSW: −4.99<br>RB: 3<br>tPSA: 55.1<br>hDon: 1<br>hAcc: 4 | 2-phenyl-2,5,6,7-tetrahydro-4H-1,2,3-benzotriazol-4-one phenylhydrazone |
| $C_{18}H_{12}BrClN_2O_4S$ | 5667469 | Inh07 | Mol Weight: 468<br>cLogP: 4.70<br>LogSW: −6.62<br>RB: 2<br>tPSA: 78.9<br>hDon: 2<br>hAcc: 4 | 5-(3-bromo-4-hydroxy-5-methoxy-benzylidene)-1-(3-chlorophenyl)-2-thioxodihydro-4,6(1H,5H)-pyrimidinedione |
| $C_{16}H_{17}NO_4$ | 5667569 | Inh08 | Mol Weight: 468<br>cLogP: 4.70<br>LogSW: −6.62<br>RB: 2<br>tPSA: 78.9<br>hDon: 2<br>hAcc: 4 | 8-(ethoxy-carbonyl)-3a,4,5,9b-tetrahydro-3H-cyclopenta[c]-quinoline-4-carboxylic acid |
| $C_{16}H_{17}NO_2S_2$ | 5668453 | Inh09 | Mol Weight: 319<br>cLogP: 3.41<br>LogSW: −3.86<br>RB: 2<br>tPSA: 40.5<br>hDon: 1<br>hAcc: 2 | 3-cyclohexyl-5-(2-hydroxybenzyl-idene)-2-thioxo-1,3-thiazolidin-4-one |

TABLE 1-continued

Chemical compounds used in the screening for inhibitors of the malt paracaspase activity.

| Structure | Chem-Bridge ID | PSB ID | Properties | MolName |
|---|---|---|---|---|
| $C_{19}H_{14}BrClN_2O_4S$ | 5670379 | Inh10 | Mol Weight: 482<br>cLogP: 5.31<br>LogSW: −7.25<br>RB: 2<br>tPSA: 67.9<br>hDon: 1<br>hAcc: 4 | 5-(2-bromo-4,5-dimethoxy-benzylidene)-1-(4-chlorophenyl)-2-thioxodihydro-4,6(1H,5H)-pyrimidinedione |
| $C_{11}H_8N_2O_3S$ | 5677476 | Inh11 | Mol Weight: 248<br>cLogP: 1.88<br>LogSW: −2.62<br>RB: 2<br>tPSA: 71.3<br>hDon: 2<br>hAcc: 3 | 5-[3-(2-furyl)-2-propen-1-ylidene]-2-thioxodi-hydro-4,6(1H,5H)-pyrimidinedione |
| $C_{18}H_{11}ClN_2O_4S$ | 5677728 | Inh12 | Mol Weight: 387<br>cLogP: 4.29<br>LogSW: −5.68<br>RB: 2<br>tPSA: 67.9<br>hDon: 1<br>hAcc: 4 | 5-(1,3-benzodioxol-5-ylmethylene)-1-(3-chlorophenyl)-2-thioxodihydro-4,6(1H,5H)-pyrimidinedione |
| $C_9H_{10}N_4S$ | 5678019 | Inh13 | Mol Weight: 206<br>cLogP: 2.19<br>LogSW: −2.58<br>RB: 1<br>tPSA: 56.7<br>hDon: 1<br>hAcc: 3 | 4-amino-5-(4-methylphenyl)-4H-1,2,4-triazole-3-thiol |
| $C_{15}H_8ClIN_2O_3S$ | 5682572 | Inh14 | Mol Weight: 459<br>cLogP: 5.02<br>LogSW: −6.83<br>RB: 2<br>tPSA: 62.6<br>hDon: 1<br>hAcc: 3 | 1-(4-chlorophenyl)-5-[(5-iodo-2-furyl)-methylene]-2-thioxodihydro-4,6(1H,5H)-pyrimidinedione |
| $C_{11}H_{16}N_2OS$ | 5685044 | Inh15 | Mol Weight: 224<br>cLogP: 2.80<br>LogSW: −3.23<br>RB: 1<br>tPSA: 69.1<br>hDon: 2<br>hAcc: 1 | 2-amino-6-ethyl-4,5,6,7-tetrahydro-1-benzothiophene-3-carboxamide |
| $C_{19}H_{22}N_2O_3S$ | 5703736 | Inh16 | Mol Weight: 358<br>cLogP: 4.30<br>LogSW: −5.49<br>RB: 3<br>tPSA: 81.4<br>hDon: 2<br>hAcc: 3 | 6-ethyl-2-[(4-methoxybenzoyl)amino]-4,5,6,7-tetrahydro-1-benzothiophene-3-carboxamide |
| $C_{17}H_{14}N_4O_3S$ | 5705921 | Inh17 | Mol Weight: 354<br>cLogP: 4.09<br>LogSW: −5.28<br>RB: 3<br>tPSA: 91.0<br>hDon: 2<br>hAcc: 4 | 4-{[(2-hydroxy-5-nitrophenyl)-amino]methylene}-5-methyl-2-phenyl-2,4-dihydro-3H-pyrazole-3-thione |
| $C_{15}H_{17}BrN_6O$ | 5733866 | Inh18 | Mol Weight: 377<br>cLogP: 2.52<br>LogSW: −4.10<br>RB: 5<br>tPSA: 98.3<br>hDon: 2<br>hAcc: 5 | 2-(4-amino-6-methoxy-1,3,5-triazin-2-yl)-1-cyclopropylethanone (4-bromophenyl) hydrazone |
| $C_{12}H_{15}N_3S$ | 5738556 | Inh19 | Mol Weight: 233<br>cLogP: 3.88<br>LogSW: −4.22<br>RB: 2<br>tPSA: 41.6<br>hDon: 1<br>hAcc: 2 | 5-(4-tert-butylphenyl)-4H-1,2,4-triazole-3-thiol |
| $C_{15}H_{13}Cl_2N_5S_2$ | 5745398 | Inh20 | Mol Weight: 398<br>cLogP: 4.94<br>LogSW: −6.32<br>RB: 4<br>tPSA: 76.2<br>hDon: 2<br>hAcc: 3 | 1-(3,4-dichlorophenyl)ethanone(2'-amino-4'-methyl-4,5'-bi-1,3-thiazol-2-yl)hydrazone |
| $C_{16}H_{14}N_4O_2S$ | 5748942 | Inh21 | Mol Weight: 326<br>cLogP: 3.44<br>LogSW: −4.52<br>RB: 4<br>tPSA: 65.4<br>hDon: 0<br>hAcc: 6 | 4-{[3-(2-furyl)-2-propen-1-ylidene]-amino}-5-(4-methoxyphenyl)-4H-1,2,4-triazole-3-thiol |
| $C_{11}H_8ClNO_3S_2$ | 5761742 | Inh22 | Mol Weight: 302<br>cLogP: 1.91<br>LogSW: −3.03<br>RB: 1<br>tPSA: 58.6<br>hDon: 2<br>hAcc: 3 | 5-(5-chloro-2-hydroxy-3-methoxybenzyl-idene)-2-thioxo-1,3-thiazolidin-4-one |
| $C_{10}H_7BrN_2O_3S$ | 5808644 | Inh23 | Mol Weight: 315<br>cLogP: 1.96<br>LogSW: −3.17<br>RB: 3<br>tPSA: 65.2<br>hDon: 0<br>hAcc: 5 | S-[5-(4-bromophenyl)-1,3,4-oxadiazol-2-yl]O-methyl thiocarbonate |
| $C_{22}H_{13}ClN_2O_5$ | | Inh24 | Mol Weight: 453<br>cLogP: 5.24<br>LogSW: −6.98<br>RB: 4<br>tPSA: 99.8<br>hDon: 2<br>hAcc: 5 | 2-chloro-4-{5-[(4,6-dioxo-1-phenyl-2-thioxotetrahydro-5(2H)-pyrimidinylidene)-methyl]-2-furyl}benzoic acid |
| $C_{17}H_{14}N_2O_4$ | 6012954 | Inh25 | Mol Weight: 310<br>cLogP: 4.19<br>LogSW: −5.04<br>RB: 2<br>tPSA: 79.6<br>hDon: 1<br>hAcc: 4 | 1-(3,5-dimethylphenyl)-5-(2-furylmethylene)-2,4,6(1H,3H,5H)-pyrimidinetrione |
| $C_9H_7N_3OS$ | 6047234 | Inh26 | Mol Weight: 205<br>cLogP: 2.45<br>LogSW: −2.79<br>RB: 1<br>tPSA: 61.5<br>hDon: 2<br>hAcc: 2 | 6-phenyl-3-thioxo-3,4-dihydro-1,2,4-triazin-5(2H)-one |
| $C_{21}H_{17}Cl_2N_3O_2S$ | 6469227 | Inh27 | Mol Weight: 446<br>cLogP: 6.12<br>LogSW: −7.68<br>RB: 3<br>tPSA: 52.6<br>hDon: 1<br>hAcc: 2 | 1-(3,4-dichlorophenyl)-5-[4-(1-pyrrolidinyl)benzylidene]-2-thioxodihydro-4,6(1H,5H)-pyrimidinedione |

REFERENCES

Baens M., S. Fevery, X. Sagaert, H. Noels, S. Hagens, V. Broeckx, A. D. Billiau, C. De Wolf-Peeters, and P. Marynen (2006). Selective Expansion of Marginal Zone B-Cells in Eμ-API2-MALT1 Mice is Linked to Enhanced IkB kinase g Polyubiquitination. *Cancer Res.* 66:5270-5277.

Bao Q. and Y. Shi (2007). Apoptosome: a platform for the activation of initiator caspases. *Cell Death Differ.* 14:56-65.

Beckett D., E. Kovaleva, and P. J. Schatz (1999). A minimal peptide substrate in biotin holoenzyme synthetase-catalyzed biotinylation. *Protein Sci.* 8:921-929.

Beyaert R., K. Heyninck and S. Van Huffel (2000). A20 and A20-binding proteins as cellular inhibitors of nuclear factor-kappa B-dependent gene expression and apoptosis. *Biochem. Pharmacol.* 60:1143-1151.

Boatright K. M., M. Renatus, F. L. Scott, S. Sperandio, H. Shin, I. M. Pedersen, J. E. Ricci, W. A. Edris, D. P. Sutherlin, D. R. Green, and G. S. Salvesen (2003). A unified model for apical caspase activation. *Mol. Cell* 11:529-541.

Boatright K. M. and G. S. Salvesen (2003). Mechanisms of caspase activation. *Curr. Opin. Cell Biol.* 15:725-731.

Boone D. L. et al. (2004). The ubiquitin-modifying enzyme A20 is required for termination of Toll-like receptor responses. *Nat. Immunol.* 5:1052-1060.

Che T. J., Y. You, D. H. Wang, M. J. Tanner, V. M. Dixit, and X. Lin (2004). MALT1/paracaspase is a signaling component downstream of CARMA1 and mediates T cell receptor-induced NF-kappa B activation. *J. Biol. Chem.* 279: 15870-15876.

Chen Z. J. (2005). Ubiquitin signaling in the NF-kappaB pathway. *Nat. Cell. Biol.* 7:758-765.

de Boer E., P. Rodriguez, E. Bonte, J. Krijgsveld, E. Katsantoni, A. Heck, F. Grosveld, and J. Strouboulis (2003). Efficient biotinylation and single-step purification of tagged transcription factors in mammalian cells and transgenic mice. *Proc. Natl. Acad. Sci. U.S.A.* 100:7480-7485.

Dierlamm J. et al. (1999). The apoptosis inhibitor gene API2 and a novel 18q gene, MLT, are recurrently rearranged in the t(11; 18)(q21; q21) associated with mucosa-associated lymphoid tissue lymphomas. *Blood* 93:3601-3609.

Earnshaw W. C., L. M. Martins, and S. H. Kaufmann (1999). Mammalian caspases: structure, activation, substrates, and functions during apoptosis. *Annu. Rev. Biochem.* 68:383-424.

Egawa T. et al. (2003). Requirement for CARMA1 in antigen receptor-induced NFkappa B activation and lymphocyte proliferation. *Curr. Biol.* 13:1252-1258.

Ferch U., C. M. Buschenfelde, A. Gewies, E. Wegener, S. Rauser, C. Peschel, D. Krappmann, and J. Ruland (2007). MALT1 directs B cell receptor-induced canonical nuclear factor-kappaB signaling selectively to the c-Rel subunit. *Nat. Immunol.* 8:984-991.

Hara H., C. Bakal, T. Wada, D. Bouchard, R. Rottapel, T. Saito, and J. M. Penninger (2004). The molecular adapter Carma1 controls entry of IkappaB kinase into the central immune synapse. *J. Exp. Med.* 200:1167-1177.

Heyninck K. et al. (1999). The zinc finger protein A20 inhibits TNF-induced NFkappaB-dependent gene expression by interfering with an RIP- or TRAF2-mediated transactivation signal and directly binds to a novel NF-kappaB-inhibiting protein ABIN. *J. Cell Biol.* 145:1471-1482.

Klemm S., J. Gutermuth, L. Hültner, T. Sparwasser, H. Behrendt, C. Peschel, T. W. Mak, T. Jakob, and J. Ruland (2006). The Bcl10-Malt1 complex segregates Fc epsilon RI-mediated nuclear factor kappa B activation and cytokine production from mast cell degranulation. *J. Exp. Med.* 203:337-347.

Klemm S., S. Zimmermann, C. Peschel, T. W. Mak, and J. Ruland (2007). Bcl10 and Malt1 control lysophosphatidic acid-induced NF-kappaB activation and cytokine production. *Proc. Natl. Acad. Sci. U.S.A.* 104:134-138.

Lee E. G. et al. (2000). Failure to regulate TNF-induced NF-kappaB and cell death responses in A20-deficient mice. *Science* 289:2350-2354.

Lee K. Y., F. D'Acquisto, M. S. Hayden, J. H. Shim, and S. Ghosh (2005). PDK1 nucleates T cell receptor-induced signaling complex for NF-kappaB activation. *Science* 308: 114-118.

Lucas P. C., M. Yonezumi, N. Inohara, L. M. McAllister-Lucas, M. E. Abazeed, F. F. Chen, S. Yamaoka, M. Seto, and G. Nunez (2001). Bcl10 and MALT1, independent targets of chromosomal translocation in MALT lymphoma, cooperate in a novel NF-kappaB signaling pathway. *J. Biol. Chem.* 276:19012-19019.

Matsumoto R., D. Wang, M. Blonska, H. Li, M. Kobayashi, B. Pappu, Y. Chen, D. Wang, and X. Lin (2005). Phosphorylation of CARMA1 plays a critical role in T Cell receptor-mediated NF-kappaB activation. *Immunity* 23:575-585.

Noels H., G. van Loo, S. Hagens, V. Broeckx, R. Beyaert, P. Marynen, and M. Baens (2007). A novel TRAF6 binding site in MALT1 defines distinct mechanisms of NF-kappa B activation by API2-MALT1 fusions. *J. Biol. Chem.* 282: 10180-10189.

Rawlings D. J., K. Sommer, and M. E. Moreno-Garcia (2006). The CARMA1 signalosome links the signaling machinery of adaptive and innate immunity in lymphocytes. *Nat. Rev. Immunol.* 6:799-812.

Ruefli-Brasse A. A., D. M. French, and V. M. Dixit (2003). Regulation of NF-kappa B-dependent lymphocyte activation and development by paracaspase. *Science* 302:1581-1584.

Ruland J., G. S. Duncan, A. Elia, I. del Barco Barrantes, L. Nguyen, S. Plyte, D. G. Millar, D. Bouchard, A. Wakeham, P. S. Ohashi, and T. W. Mak (2001). Bcl10 is a positive regulator of antigen receptor-induced activation of NF-kappaB and neural tube closure. *Cell* 104:33-42.

Ruland J., G. S. Duncan, A. Wakeham, and T. W. Mak (2003). Differential Requirement for Malt1 in T and B Cell Antigen Receptor Signaling. *Immunity* 19:749-758.

Sanchez-Izquierdo D. et al. (2003). MALT1 is deregulated by both chromosomal translocation and amplification in B-cell non-Hodgkin lymphoma. *Blood* 101:4539-4546.

Shambharkar P. B., M. Blonska, B. P. Pappu, H. Li, Y. You, H. Sakurai, B. G. Darnay, H. Hara, J. Penninger, and X. Lin (2007). Phosphorylation and ubiquitination of the IkappaB kinase complex by two distinct signaling pathways. *EMBO J.* 26:1794-1805.

Snipas S. J. et al. (2004). Characteristics of the caspase-like catalytic domain of human paracaspase. *Biol. Chem.* 385: 1093-1098.

Sommer K., B. Guo, J. L. Pomerantz, A. D. Bandaranayake, M. E. Moreno-Garcia, Y. L. Ovechkina, and D. J. Rawlings (2005). Phosphorylation of the CARMA1 linker controls NF-kappaB activation. *Immunity* 23:561-574.

Stilo R., D. Liguoro, J. B. Di, S. Formisano, E. Consiglio, A. Leonardi, and P. Vito (2004). Physical and functional interaction of CARMA1 and CARMA3 with Ikappa kinase gamma-NFkappaB essential modulator. *J. Biol. Chem.* 279:34323-34331.

Su T. T. et al. (2002). PKC-beta controls I kappa B kinase lipid raft recruitment and activation in response to BCR signaling. *Nat. Immunol.* 3:780-786.

Sun Z. et al. (2000). PKC-theta is required for TCR-induced NF-kappaB activation in mature but not immature T lymphocytes. *Nature* 404:402-407.

Sun L. J., L. Deng, C. K. Ea, Z. P. Xia, and Z. J. J. Chen (2004). The TRAF6 ubiquitin ligase and TAK1 kinase mediate IKK activation by BCL10 and MALT1 in T lymphocytes. *Mol. Cell* 14:289-301.

Tewari M. et al. (1995). Lymphoid expression and regulation of A20, an inhibitor of programmed cell death. *J. Immunol.* 154:1699-1706.

Uren G. A., K. O'Rourke, L. Aravind, T. M. Pisabarro, S. Seshagiri, V. E. Koonin, and M. V. Dixit (2000). Identification of paracaspases and metacaspases: two ancient families of caspase-like proteins, one of which plays a key role in MALT lymphoma. *Mol. Cell* 6:961-967.

Vercammen D., B. Van de Cotte, G. De Jaeger, D. Eeckhout, P. Casteels, K. Vandepoele, I. Vandenberghe, J. Van Beeumen, D. Inze, and F. Van Breusegem (2004). Type II metacaspases Atmc4 and Atmc9 of *Arabidopsis thaliana* cleave substrates after arginine and lysine. *J. Biol. Chem.* 279:45329-45336.

Vercammen D., B. Belenghi, B. van de Cotte, T. Beunens, J. A. Gavigan, R. De Rycke, A. Brakenier, D. Inzé, J. L. Harris, and F. Van Breusegem (2006). Serpin 1 of *Arabidopsis thaliana* is a suicide inhibitor of matacaspase 9. *J. Mol. Biol.* 364:625-636.

Wang D., Y. You, S. M. Case, L. M. McAllister-Lucas, L. Wang, P. S. DiStefano, G. Nunez, J. Bertin, and X. Lin (2002). A requirement for CARMA1 in TCR-induced NF-kappa B activation. *Nat. Immunol.* 3:830-835.

Wang D., R. Matsumoto, Y. You, T. Che, X. Y. Lin, S. L. Gaffen, and X. Lin (2004). CD3/CD28 Costimulation-Induced NF-kappaB Activation Is Mediated by Recruitment of Protein Kinase C-theta, Bcl10, and I-kappaB Kinase beta to the Immunological Synapse through CARMA1. *Mol. Cell. Biol.* 24:164-171.

Wegener E. and D. Krappmann (2007). CARD-Bcl10-Malt1 signalosomes: missing link to NF-kappaB. *Sci. STKE.* 384: pe21.

Wertz I. E. et al. (2004). De-ubiquitination and ubiquitin ligase domains of A20 down-regulate NF-kappaB signaling. *Nature* 430:694-699.

Willis T. G. et al. (1999). Bcl10 is involved in t(1; 14)(p22; q32) of MALT B cell lymphoma and mutated in multiple tumor types. *Cell* 96:35-45.

Wu C. J., D. B. Conze, T. Li, S. M. Srinivasula, and J. D. Ashwell (2006). NEMO is a sensor of Lys 63-linked polyubiquitination and functions in NF-kappaB activation. *Nat. Cell Biol.* 8:398-406.

Zhang Q. et al. (1999). Inactivating mutations and overexpression of BCL10, a caspase recruitment domain-containing gene, in MALT lymphoma with t(1; 14)(p22; q32). *Nat. Genet.* 22:63-68.

Zhou H. L., I. Wertz, K. O'Rourke, M. Ultsch, S. Seshagiri, M. Eby, W. Xiao, and V. M. Dixit (2004). Bcl10 activates the NF-kappa B pathway through ubiquitination of NEMO. *Nature* 427:167-171.

---

The invention claimed is:

1. An inhibitor of the MALT1 proteolytic or autoproteolytic activity, wherein said inhibitor is selected from the group consisting of Z-LSSR-CHO, Z-LSSR-CMK, Z-GASR-CHO, and Z-GASR-CMK.

2. A medicament comprising: the inhibitor of claim 1.

3. A method of treating marginal zone lymphoma in a subject comprising administering a compound of claim 1 to the subject.

* * * * *

SEQUENCE LISTING

```
<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: Peptide derivative

<400> SEQUENCE: 1

Leu Ser Ser Arg
1

<210> SEQ ID NO 2
<211> LENGTH: 4
<212> TYPE: PRT
<213> ORGANISM: Artificial Sequence
<220> FEATURE:
<223> OTHER INFORMATION: Peptide derivative

<400> SEQUENCE: 2

Gly Ala Ser Arg
1

<210> SEQ ID NO 3
<211> LENGTH: 12
<212> TYPE: PRT
<213> ORGANISM: Artificial Sequence
<220> FEATURE:
<223> OTHER INFORMATION: Myristoylation/palmytoylation (mp) motif of Lck

<400> SEQUENCE: 3

Met Gly Cys Val Cys Ser Ser Asn Pro Glu Asp Asp
1               5                   10

<210> SEQ ID NO 4
<211> LENGTH: 15
<212> TYPE: PRT
<213> ORGANISM: Artificial Sequence
```

```
<220> FEATURE:
<223> OTHER INFORMATION: Avi-tag sequence

<400> SEQUENCE: 4

Gly Leu Asn Asp Ile Phe Glu Ala Gln Lys Ile Glu Trp His Glu
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Flexible linker

<400> SEQUENCE: 5

Ser Gly Ser Ser Gly Ser Ser Gly
1               5

<210> SEQ ID NO 6
<211> LENGTH: 69
<212> TYPE: PRT
<213> ORGANISM: Artificial
<220> FEATURE:
<223> OTHER INFORMATION: Figure 8: A20

<400> SEQUENCE: 6

Glu Arg Arg Gln Lys Asn Gln Asn Lys Leu Pro Lys Leu Asn Ser Lys
1               5                   10                  15

Pro Gly Pro Glu Gly Leu Pro Gly Met Ala Leu Gly Ala Ser Arg Gly
            20                  25                  30

Glu Ala Tyr Glu Pro Leu Ala Trp Asn Pro Glu Glu Ser Thr Gly Gly
        35                  40                  45

Pro His Ser Ala Pro Pro Thr Ala Pro Ser Pro Phe Leu Phe Ser Glu
    50                  55                  60

Thr Thr Ala Met Lys
65

<210> SEQ ID NO 7
<211> LENGTH: 69
<212> TYPE: PRT
<213> ORGANISM: Artificial
<220> FEATURE:
<223> OTHER INFORMATION: Figure 8: A20-R410/411A

<400> SEQUENCE: 7

Glu Ala Ala Gln Lys Asn Gln Asn Lys Leu Pro Lys Leu Asn Ser Lys
1               5                   10                  15

Pro Gly Pro Glu Gly Leu Pro Gly Met Ala Leu Gly Ala Ser Arg Gly
            20                  25                  30

Glu Ala Tyr Glu Pro Leu Ala Trp Asn Pro Glu Glu Ser Thr Gly Gly
        35                  40                  45

Pro His Ser Ala Pro Pro Thr Ala Pro Ser Pro Phe Leu Phe Ser Glu
    50                  55                  60

Thr Thr Ala Met Lys
65

<210> SEQ ID NO 8
<211> LENGTH: 69
<212> TYPE: PRT
<213> ORGANISM: Artificial
<220> FEATURE:
<223> OTHER INFORMATION: Figure 8: A20-R439A

<400> SEQUENCE: 8
```

-continued

```
Glu Arg Arg Gln Lys Asn Gln Asn Lys Leu Pro Lys Leu Asn Ser Lys
1               5                   10                  15

Pro Gly Pro Glu Gly Leu Pro Gly Met Ala Leu Gly Ala Ser Ala Gly
                20                  25                  30

Glu Ala Tyr Glu Pro Leu Ala Trp Asn Pro Glu Glu Ser Thr Gly Gly
            35                  40                  45

Pro His Ser Ala Pro Pro Thr Ala Pro Ser Pro Phe Leu Phe Ser Glu
        50                  55                  60

Thr Thr Ala Met Lys
65

<210> SEQ ID NO 9
<211> LENGTH: 21
<212> TYPE: DNA
<213> ORGANISM: Artificial
<220> FEATURE:
<223> OTHER INFORMATION: siRNA for MALT1

<400> SEQUENCE: 9
aaggtactgg agcctgaagg a                                           21

<210> SEQ ID NO 10
<211> LENGTH: 21
<212> TYPE: DNA
<213> ORGANISM: Artificial
<220> FEATURE:
<223> OTHER INFORMATION: siRNA for MALT1

<400> SEQUENCE: 10
aaggttgcac agtcacagaa t                                           21

<210> SEQ ID NO 11
<211> LENGTH: 21
<212> TYPE: DNA
<213> ORGANISM: Artificial
<220> FEATURE:
<223> OTHER INFORMATION: siRNA for BCL10

<400> SEQUENCE: 11
aagggctgga aaattgttag a                                           21

<210> SEQ ID NO 12
<211> LENGTH: 21
<212> TYPE: DNA
<213> ORGANISM: Artificial
<220> FEATURE:
<223> OTHER INFORMATION: siRNA for BCL10

<400> SEQUENCE: 12
aaggactaaa atgtagcagt t                                           21

<210> SEQ ID NO 13
<211> LENGTH: 25
<212> TYPE: DNA
<213> ORGANISM: Artificial
<220> FEATURE:
<223> OTHER INFORMATION: siRNA for Jurkat cells

<400> SEQUENCE: 13
cctgtgaaat agtactgcac ttaca                                       25

<210> SEQ ID NO 14
<211> LENGTH: 25
<212> TYPE: DNA
```

```
<213> ORGANISM: Artificial
<220> FEATURE:
<223> OTHER INFORMATION: siRNA for Jurkat cells

<400> SEQUENCE: 14
cactctgaag taagagcaat gggaa                                          25

<210> SEQ ID NO 15
<211> LENGTH: 4
<212> TYPE: PRT
<213> ORGANISM: Artificial Sequence
<220> FEATURE:
<223> OTHER INFORMATION: Peptide derivative

<400> SEQUENCE: 15

Leu Cys Cys Arg
1

<210> SEQ ID NO 16
<211> LENGTH: 4
<212> TYPE: PRT
<213> ORGANISM: Artificial Sequence
<220> FEATURE:
<223> OTHER INFORMATION: Mutant serpin

<400> SEQUENCE: 16

Ile Lys Leu Ala
1
```